(12) United States Patent
Watson et al.

(10) Patent No.: US 11,647,953 B2
(45) Date of Patent: May 16, 2023

(54) HAIR RATCHETING ELECTROENCEPHALOGRAM SENSORS

(71) Applicant: X Development LLC, Mountain View, CA (US)

(72) Inventors: Philip Edwin Watson, Santa Cruz, CA (US); Gabriella Levine, San Francisco, CA (US); Sarah Ann Laszlo, Mountain View, CA (US)

(73) Assignee: X Development LLC, Mountain View, CA (US)

( * ) Notice: Subject to any disclaimer, the term of this patent is extended or adjusted under 35 U.S.C. 154(b) by 1500 days.

(21) Appl. No.: 15/891,740

(22) Filed: Feb. 8, 2018

(65) Prior Publication Data

US 2019/0239807 A1    Aug. 8, 2019

(51) Int. Cl.
*A61B 5/291* (2021.01)
*A61B 5/00* (2006.01)
*A61B 5/375* (2021.01)
*A61B 5/378* (2021.01)

(52) U.S. Cl.
CPC .......... *A61B 5/6814* (2013.01); *A61B 5/0006* (2013.01); *A61B 5/291* (2021.01); *A61B 5/375* (2021.01); *A61B 5/378* (2021.01); *A61B 5/6838* (2013.01); *A61B 2562/0209* (2013.01)

(58) Field of Classification Search
CPC ....... A61B 5/6814; A61B 5/291; A61B 5/375; A61B 5/378; A61B 5/0006; A61B 5/6838; A61B 2562/0209
See application file for complete search history.

(56) References Cited

U.S. PATENT DOCUMENTS

| 1,230,921 | A |   | 6/1917  | Paul |
|-----------|---|---|---------|------|
| 3,469,577 | A | * | 9/1969  | Kater ...................... A61N 1/04 600/397 |
| 4,125,110 | A |   | 11/1978 | Hymes |
| 4,632,122 | A |   | 12/1986 | Johansson et al. |
| 4,709,702 | A |   | 12/1987 | Sherwin |
| D327,325  | S |   | 6/1992  | Strand |

(Continued)

FOREIGN PATENT DOCUMENTS

WO    WO 2018068013    4/2018

OTHER PUBLICATIONS

Mcnall, "How do you clean a patient's head after removing EEG electrodes?" ASET Department of Education Report, retrieved from URL <https://asetdeptedu.blogspot.com/2014/04/how-do-you-clean-patients-head-after.html>, Apr. 17, 2014, retrieved Apr. 17, 2020, 3 pages.

(Continued)

*Primary Examiner* — Adam Z Minchella
(74) *Attorney, Agent, or Firm* — Fish & Richardson P.C.

(57) ABSTRACT

A sensor device includes a sensor housing defining a channel extending along a channel axis through the housing from a first side of the sensor housing to a second side of the sensor housing opposite the first side, at least one contact electrode extending from the first side of the housing, an electrically-conducting lead attached to the housing in electrical communication with the at least one contact electrode, and a locking mechanism located in the channel permitting one-way axial motion of a thread threaded through the channel from the first side to the second side.

20 Claims, 14 Drawing Sheets

(56) References Cited

U.S. PATENT DOCUMENTS

| | | |
|---|---|---|
| 5,273,037 A | 12/1993 | Itil et al. |
| 5,404,875 A | 4/1995 | Gevins et al. |
| D369,667 S | 5/1996 | Vincents et al. |
| D378,614 S | 3/1997 | Jensen |
| D385,037 S | 10/1997 | Jensen |
| 5,823,832 A | 10/1998 | Das |
| D429,337 S | 8/2000 | Sanfilippo |
| 6,175,753 B1 | 1/2001 | Menkes et al. |
| 6,574,513 B1 | 6/2003 | Collura et al. |
| D478,173 S | 8/2003 | Nielsen |
| D478,668 S | 8/2003 | Epstein |
| 6,640,122 B2 | 10/2003 | Manoli et al. |
| 6,998,031 B1 | 2/2006 | Hill |
| D536,673 S | 2/2007 | Silber |
| D567,374 S | 4/2008 | Reznik |
| D625,823 S | 10/2010 | Schneider et al. |
| 8,112,141 B2 | 2/2012 | Wilson et al. |
| 9,055,927 B2 | 6/2015 | Nierenberg et al. |
| 9,186,084 B2 | 11/2015 | Chai et al. |
| 9,232,922 B2 | 1/2016 | Nierenberg et al. |
| 9,314,184 B2 | 4/2016 | Chai et al. |
| 9,314,185 B2 | 4/2016 | Chai et al. |
| D758,595 S | 6/2016 | Zhao |
| D768,096 S | 10/2016 | Fleischer |
| D783,818 S | 4/2017 | Hermann et al. |
| D791,956 S | 7/2017 | Stewart |
| 10,716,487 B2 | 7/2020 | Laszlo et al. |
| 10,722,134 B2 | 7/2020 | Watson et al. |
| 2001/0044573 A1 | 11/2001 | Manoli et al. |
| 2002/0029005 A1* | 3/2002 | Levendowski ...... A61B 5/6804 600/545 |
| 2002/0052610 A1 | 5/2002 | Skakoon et al. |
| 2005/0192594 A1 | 9/2005 | Skakoon et al. |
| 2007/0255127 A1 | 11/2007 | Mintz et al. |
| 2008/0269842 A1 | 10/2008 | Giftakis et al. |
| 2010/0100001 A1 | 4/2010 | Aguilar et al. |
| 2011/0046503 A1 | 2/2011 | Pradeep et al. |
| 2011/0125046 A1 | 5/2011 | Burton et al. |
| 2012/0035441 A1 | 2/2012 | Shoshihara et al. |
| 2013/0110212 A1 | 5/2013 | Feng et al. |
| 2013/0310676 A1* | 11/2013 | Jung ............... A61B 5/6843 600/383 |
| 2014/0051961 A1* | 2/2014 | Badower ............ A61B 5/369 600/383 |
| 2014/0316230 A1 | 10/2014 | Denison et al. |
| 2014/0347265 A1 | 11/2014 | Aimone et al. |
| 2015/0065838 A1 | 3/2015 | Wingeier et al. |
| 2015/0327789 A1 | 11/2015 | Sjaaheinn |
| 2015/0374255 A1 | 12/2015 | Vasapollo |
| 2016/0074649 A1* | 3/2016 | Williams .......... A61B 5/6814 607/139 |
| 2016/0228693 A1 | 8/2016 | Vardiman |
| 2017/0100300 A1* | 4/2017 | Rapp ................. A61B 5/6828 |
| 2018/0085573 A1 | 3/2018 | Alam |
| 2019/0192030 A1 | 6/2019 | Watson et al. |
| 2019/0192031 A1 | 6/2019 | Laszlo et al. |
| 2019/0192075 A1 | 6/2019 | Kranz |
| 2019/0192078 A1 | 6/2019 | Sargent et al. |
| 2019/0239763 A1 | 8/2019 | Block et al. |

OTHER PUBLICATIONS

Berg et al. "The Cyberlink Interface: Development of a Hands-Free Continuous/Discrete Mutli-Channel Computer Input Device," United Stated Air Force Research Laboratory, AFRL-HE-WP-TR-1999-0191, Feb. 1999, 63 pages.

Hasan et al. "Prediction of Epileptic Seizure by Analysing Time Series EEG Signal Using k-NN Classifier," Applied Bionics and Biomechanics, Aug. 2017, 12 pages.

Krishnan et al. "ActiveClean: an Interactive Data Clearning Framework for Modern Machine Learning," SIGMOD, Jun. 2016, 4 pages.

Liao et al. "Gaming control using a wearable and wireless Eeg-based brain-computer interface device with novel dry foam-based sensors," Journal of NeuroEngineering and Rehabilitation, 9(5), Jan. 28, 2012, 12 pages.

Ries et al. "Response-Locked Brain Dynamics of Word Production," PLoS One, 8(3), Mar. 12, 2013, 14 pages.

Telpaz et al. "Using EEG to predict consumers' future choices," Journal of Marketing Research, 52(4), Aug. 2015, 60 pages.

www.frontiernerds.com' [online] "How to Hack Toy EEGs," Apr. 7, 2010, [retrieved on Aug. 12, 2018] Retreived from Internet: URL<http://www.frontiernerds.com/brain-hack> 86 pages.

* cited by examiner

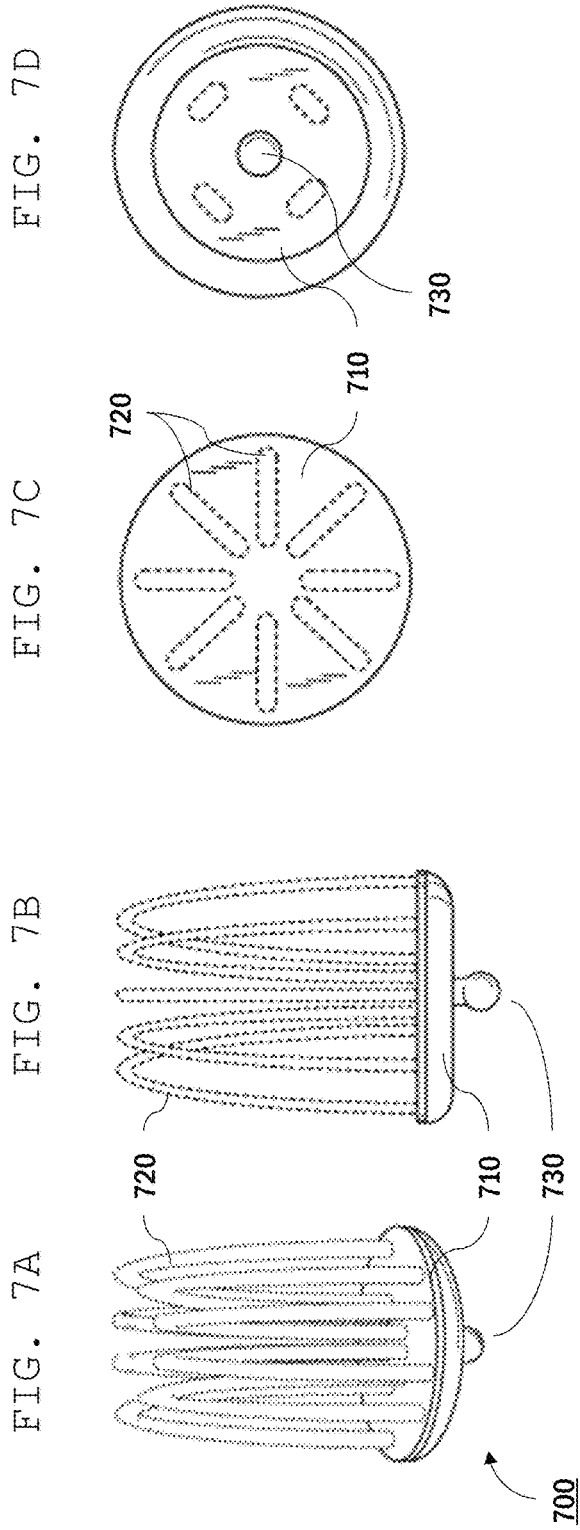
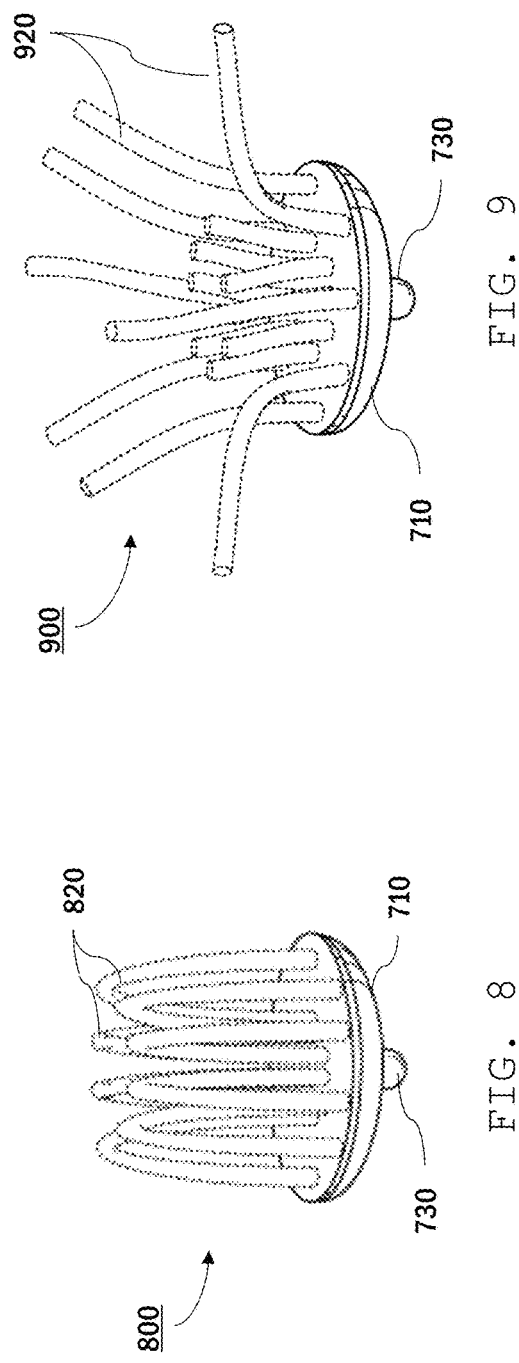

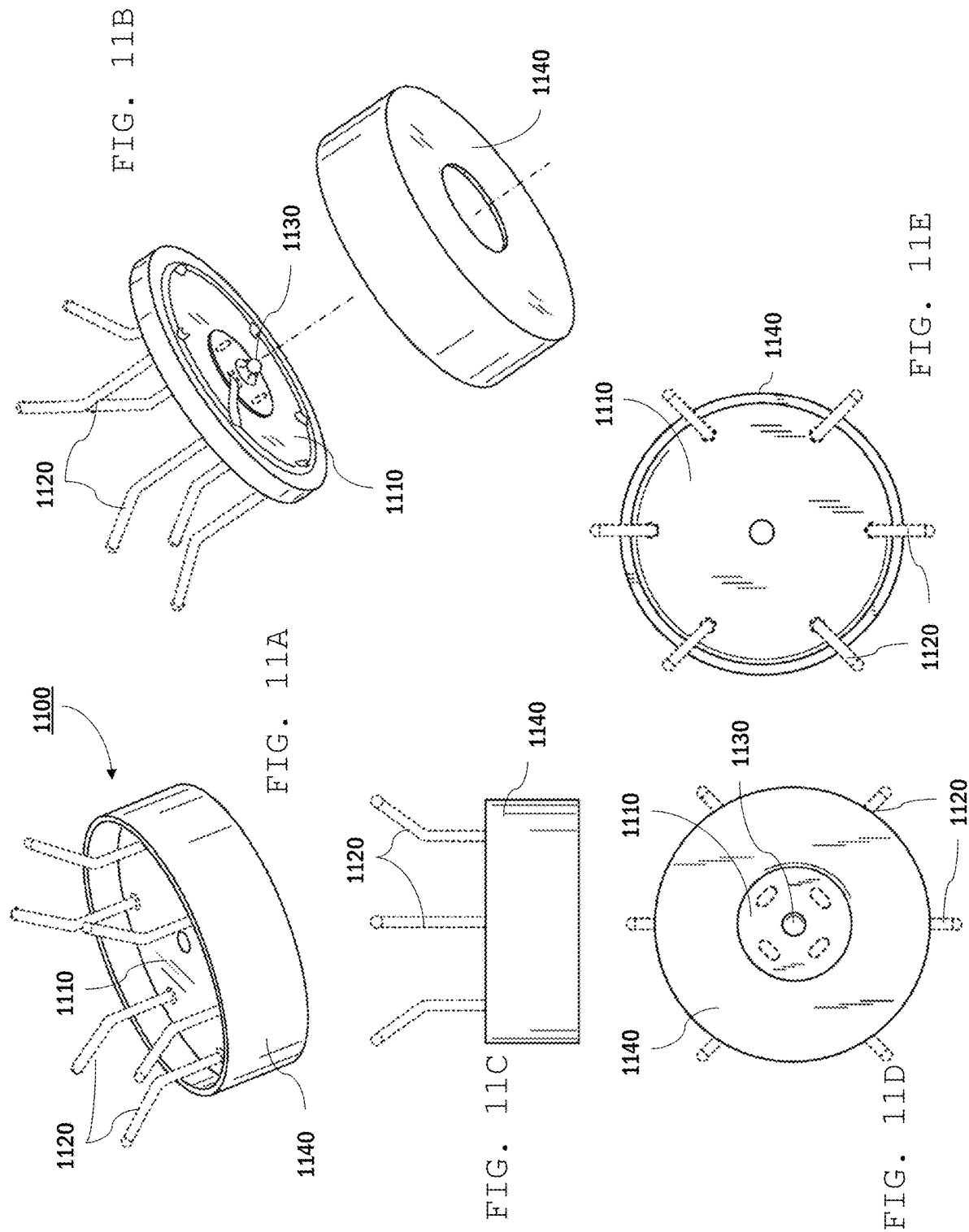

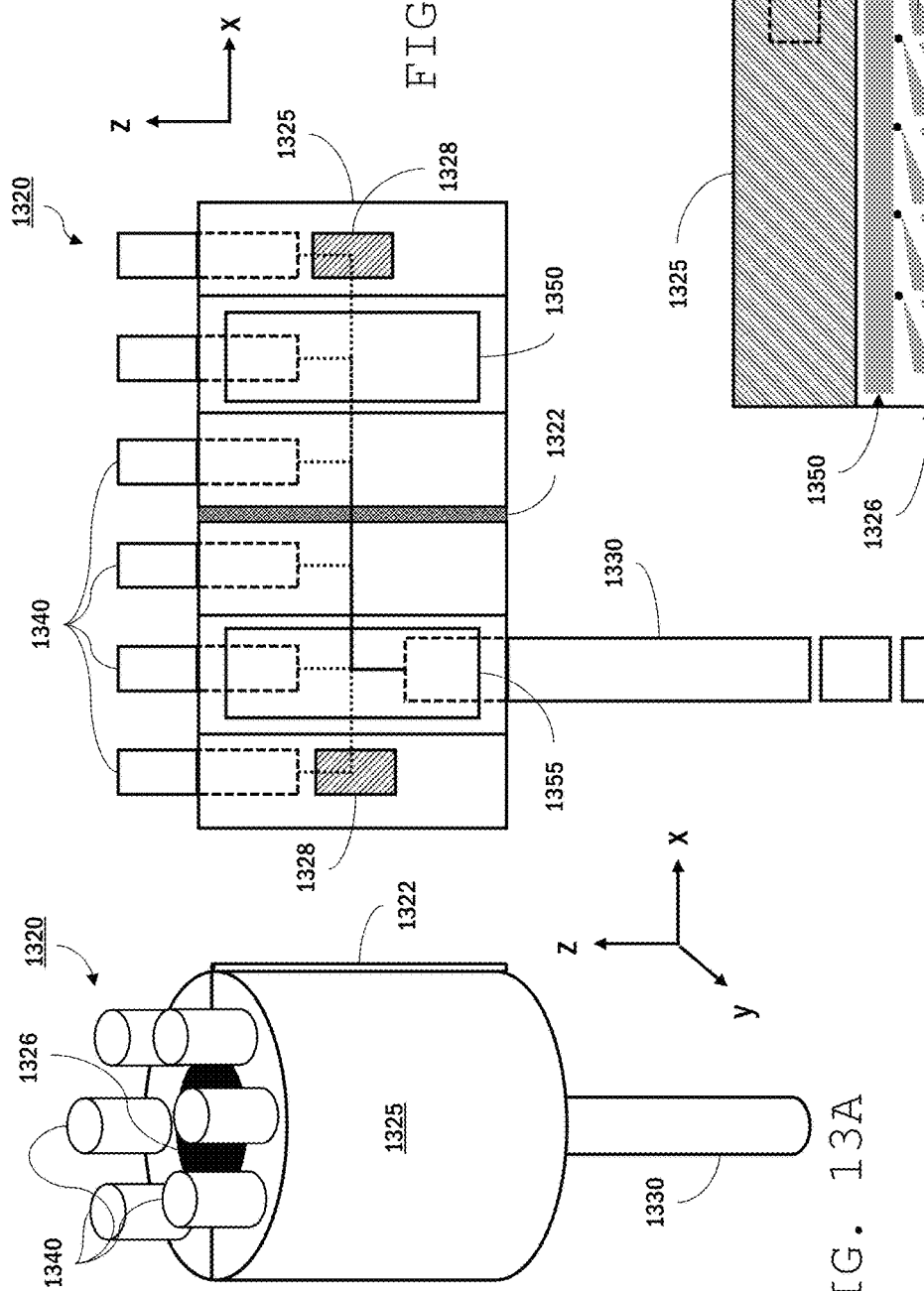
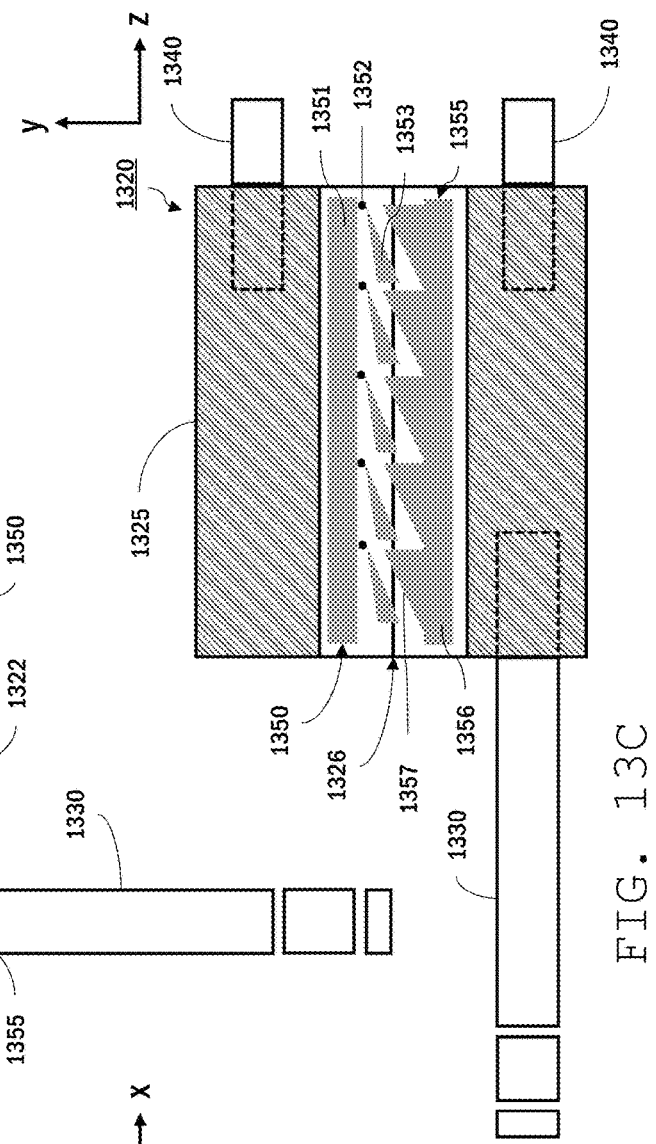
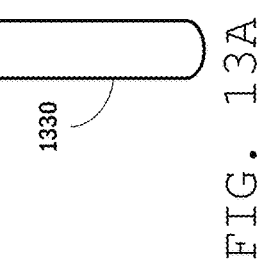
FIG. 13A
FIG. 13B
FIG. 13C

HAIR RATCHETING ELECTROENCEPHALOGRAM SENSORS

FIELD

This specification relates generally to electroencephalogram (EEG) systems, and more specifically to sensors for EEG systems.

BACKGROUND

An electroencephalogram (EEG) is a measurement that detects electrical activity in a person's brain. EEG measures the electrical activity of large, synchronously firing populations of neurons in the brain with electrodes placed on the scalp.

EEG researchers have investigated brain activity using the event-related potential (ERP) technique, in which a large number of experimental trials are time-locked and then averaged together, allowing the investigator to probe sensory, perceptual, and cognitive processing with millisecond precision. However, such EEG experiments are typically administered in a laboratory environment by one or more trained technicians. EEG administration often involves careful application of multiple sensor electrodes to a person's scalp, acquiring EEG signals using specialized and complex equipment, and offline EEG signal analysis by a trained individual.

SUMMARY

This specification describes technologies for EEG signal processing in general, and specifically to sensors for EEG systems that can provide consistent, good electrical contact between the EEG sensor and the user's skin. For example, in certain embodiments, EEG sensor devices grip locks of the user's hair to anchor itself against the user's scalp. The devices can feature a mechanical or electromechanical mechanism that allows hair to be threaded through a channel in one direction only.

In general, in a first aspect, the invention features a sensor device that includes a sensor housing defining a channel extending along a channel axis through the housing from a first side of the sensor housing to a second side of the sensor housing opposite the first side, at least one contact electrode extending from the first side of the housing, an electrically-conducting lead attached to the housing in electrical communication with the at least one contact electrode, and a locking mechanism located in the channel permitting one-way axial motion of a thread threaded through the channel from the first side to the second side.

Embodiments of the sensor device can include one or more of the following features. For example, the locking mechanism can include a ratchet. In some embodiments, the ratchet is a linear ratchet. The linear ratchet can include a rack of teeth and one or more pawls that engage the rack of teeth to permit relative motion between the rack of teeth and the thread in one direction and limit relative motion between the rack of teeth and the thread in an opposite direction. Each of the teeth can have a first surface with a first slope with respect to the axial direction and a second surface with a second slope with respect to the axial direction, the first slope being greater than the second slope.

In some embodiments, the ratcheting device is a rotary ratchet. The rotary ratchet can include at least one gear configured to rotate in about a rotary axis orthogonal to the channel axis and at least one pawl arranged to engage the gear to permit the gear to rotate in one direction of rotation and limit rotation in an opposite direction of rotation.

The device can include a mechanical release switch arranged to disengage components of the ratchet to permit axial motion of the thread through the channel from the second side to the first side.

The locking mechanism comprises an electromechanical actuator arranged to engage the thread and translate the device relative to the thread. The electromechanical actuator can include a piezoelectric actuator. The electromechanical actuator can be a linear actuator or a rotary actuator. The device can include a sensor for monitoring contact between the at least one contact electrode and a user's scalp and an electronic processor in communication with the sensor and the electromechanical actuator, the electronic processor being programmed to adjust a position of the sensor device along the thread based on the monitored contact. The electronic processor can be programmed to adjust the position to maintain a level of electrical contact between the at least one contact electrode and the user's scalp.

The at least one contact electrode can include a plurality of spatially-separated electrical contact points. The plurality of spatially-separated electrical contact points are electrically connected in parallel to the electrically-conducting lead.

The device can include a release mechanism for releasing the locking mechanism to permit disengagement of the sensor device from the thread.

In a further aspect, the invention features a system that includes a bioamplifier and the sensor device in communication with the bioamplifier via the electrically-conducting lead.

Among other advantages, the systems include portable, robust bioamplifiers that can provide real-time analysis of EEG signals under conditions that would typically result in significant signal noise and therefore be unusable or more difficult to use with other systems. For example, the systems can incorporate machine learning models that clean amplified EEG signals in real time to reduce signal noise. The machine learning models can be implemented on the same chip or hardware that performs EEG signal acquisition. The bioamplifiers can also analyze the EEG signals in real-time.

In some embodiments, the systems can provide real-time EEG analysis facilitating user interaction with a digital environment. For example, EEG systems can incorporate machine learning models that interpret EEG signals associated with information presented to the user by a computer device (e.g., a mobile device or personal computer). Accordingly, a user can use the disclosed systems to interact with a computer device using only their brain activity.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 7A is a perspective view of an embodiment of a sensor electrode including multiple wire loops.

FIG. 7B is a side view of the sensor electrode shown in FIG. 7A.

FIG. 7C is a top view of the sensor electrode shown in FIG. 7A.

FIG. 7D is a bottom view of the sensor electrode shown in FIG. 7A.

FIG. 8 is a perspective view of another embodiment of a sensor electrode including multiple wire loops.

FIG. 9 is a perspective view of an embodiment of a sensor electrode that includes wires of differing lengths.

FIG. 11A is a perspective view of an embodiment of a sensor electrode that includes a protective collar.

FIG. 11B is an exploded perspective view of the sensor electrode shown in FIG. 11A.

FIG. 11C is a side view of the sensor electrode shown in FIG. 11A.

FIG. 11D is a bottom view of the sensor electrode shown in FIG. 11A.

FIG. 11E is a top view of the sensor electrode shown in FIG. 11A.

FIG. 13A is a perspective view of an embodiment of a hair ratcheting sensor.

FIG. 13B is a plan view of the hair ratcheting sensor shown in FIG. 13A.

FIG. 13C is a cross-sectional view of the hair ratcheting sensor shown in FIG. 13A.

Like reference numbers and designations in the various drawings indicate like elements.

DETAILED DESCRIPTION

Figure 1:
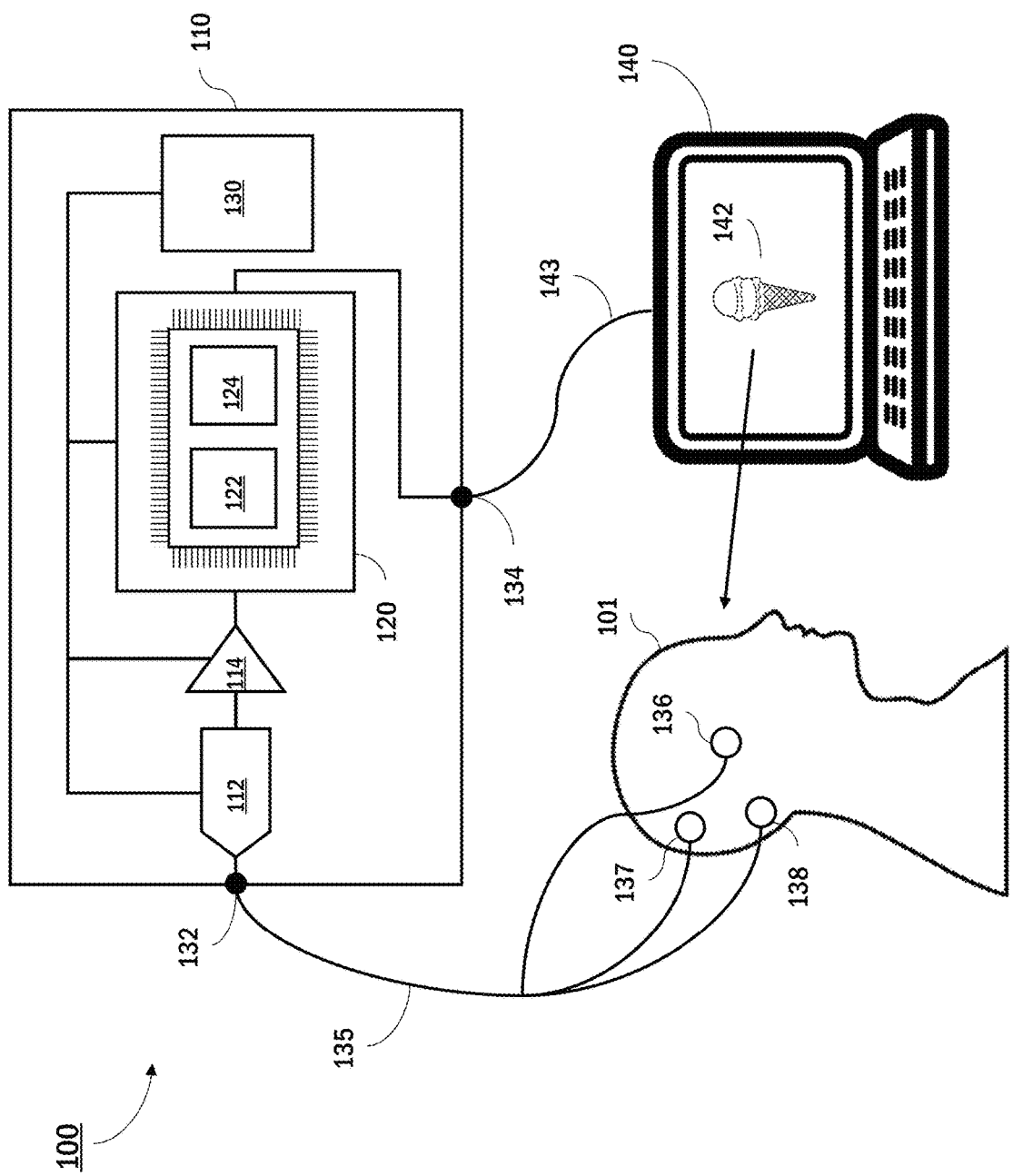
FIG. 1 is a schematic diagram of an embodiment of an EEG system.

Referring to FIG. 1, an EEG system 100 features a portable bioamplifier 110 that collects and analyzes EEG signals from a user 101 using electrode sensors 136, 137, and 138 attached to user 101's scalp. Bioamplifier 110 is in communication with a personal computer 140 which displays information 142—in this instance an image of an ice cream cone—to user 101. Bioamplifier 110 synchronously collects EEG signals from user 101 while displaying information 142 and analyzes the EEG signals, interpreting in real time user 101's brain activity responsive to viewing the information.

In certain embodiments, bioamplifier 110 is a high-impedance, low-gain amplifier with a high dynamic range. The bioamplifier impedance may be, for example, higher than 10 megaohms (e.g., 12 M$\Omega$ or more, 15 M$\Omega$ or more, 20 M$\Omega$ or more) with a maximum gain of 24× amplification. The dynamic range of bioamplifier 110 should be sufficient to acquire the entire voltage range of typical EEG signals (e.g., 0.1 to 200 μV over frequency ranges of 1 to 100 Hz). As a portable unit, bioamplifier 110 is housed within a compact, robust casing, providing a package that can be readily carried by user 101, sufficiently robust to remain functional in non-laboratory settings.

Electrode sensors 136, 137, and 138 may be dry sensors or may be placed in contact with the user's scalp using a gel. The sensors can be secured in place using, for example, adhesive tape, a headband, or some other headwear. One of sensors 136, 137, and 138 is an active sensor. Generally, the active sensor's location on the user's scalp depends on the location of brain activity of interest. In some implementations, the active sensor is placed at the back of the user's head, at or close to the user's inion. Another one of the sensors is a reference sensor. The EEG signal typically corresponds to measured electrical potential differences between the active sensor and the reference sensor. The third sensor is a ground sensor. Typically, the ground sensor is used for common mode rejection and can reduce (e.g., prevent) noise due to certain external sources, such as power line noise. In some implementations, the ground and/or reference sensors are located behind the user's ears, on the user's mastoid process.

Bioamplifier 110 includes jacks 132 and 134 for connecting leads 135 and 143 to the electrode sensors and personal computer 140, respectively. Bioamplifier 110 further includes an analogue-to-digital converter 112, an amplifier 114, and a processing module 120. Although depicted as a single analogue-to-digital converter and a single amplifier, analogue-to-digital converter 112 and amplifier 114 may each have multiple channels, capable of converting and amplifying each EEG signal separately. A power source 130 (e.g., a battery, a solar panel, a receiver for wireless power transmission) is also contained in bioamplifier 110 and is electrically connected to ADC 112, amplifier 114, and processing module 120. In general, analogue-to-digital converter 112 and amplifier 114 are selected to yield digital signals of sufficient amplitude to be processed using processing module 120.

Processing module 120 includes one or more computer processors programmed to analyze and clean amplified EEG signals received from amplifier 114 in real time. The computer processors can include commercially-available processors (e.g., a raspberry pi micro-controller) and/or custom components. In some embodiments, processing module 120 includes one or more processors custom designed for neural network computations (e.g., Tensor Processing Unit from Google or Intel Nervanna NNP from Intel Corp.). Generally, processing module 120 should include sufficient computing power to enable real time cleaning and analysis of the EEG signals.

The components of processing module 120 are selected and programmed to include two machine learning (ML) models: a ML cleaning model 122 and a ML two-choice decision model 124. ML cleaning model 122 receives raw EEG signals from amplifier 114 and, by application of a machine learning algorithm, cleans the signals to reduce noise. Thus, ML cleaning model 122 outputs cleaned EEG signals that have a reduced signal-to-noise ratio as compared with the input signals. Cleaning the EEG signal includes various operations that improve the usability of the signal for subsequent analysis, e.g., by reducing noise in the EEG signal. For example, cleaning the EEG signal can include filtering the signal by applying a transfer function to input data, e.g., to attenuate some frequencies in the data and leave others behind. Other signal cleaning operations are also possible. For example, signals can be cleaned using a neural network. Cleaning can also include operations to improve signal quality besides removal of undesirable frequencies. For instance, cleaning can include removing blinks, which digital filtering alone does not do.

Figure 2:
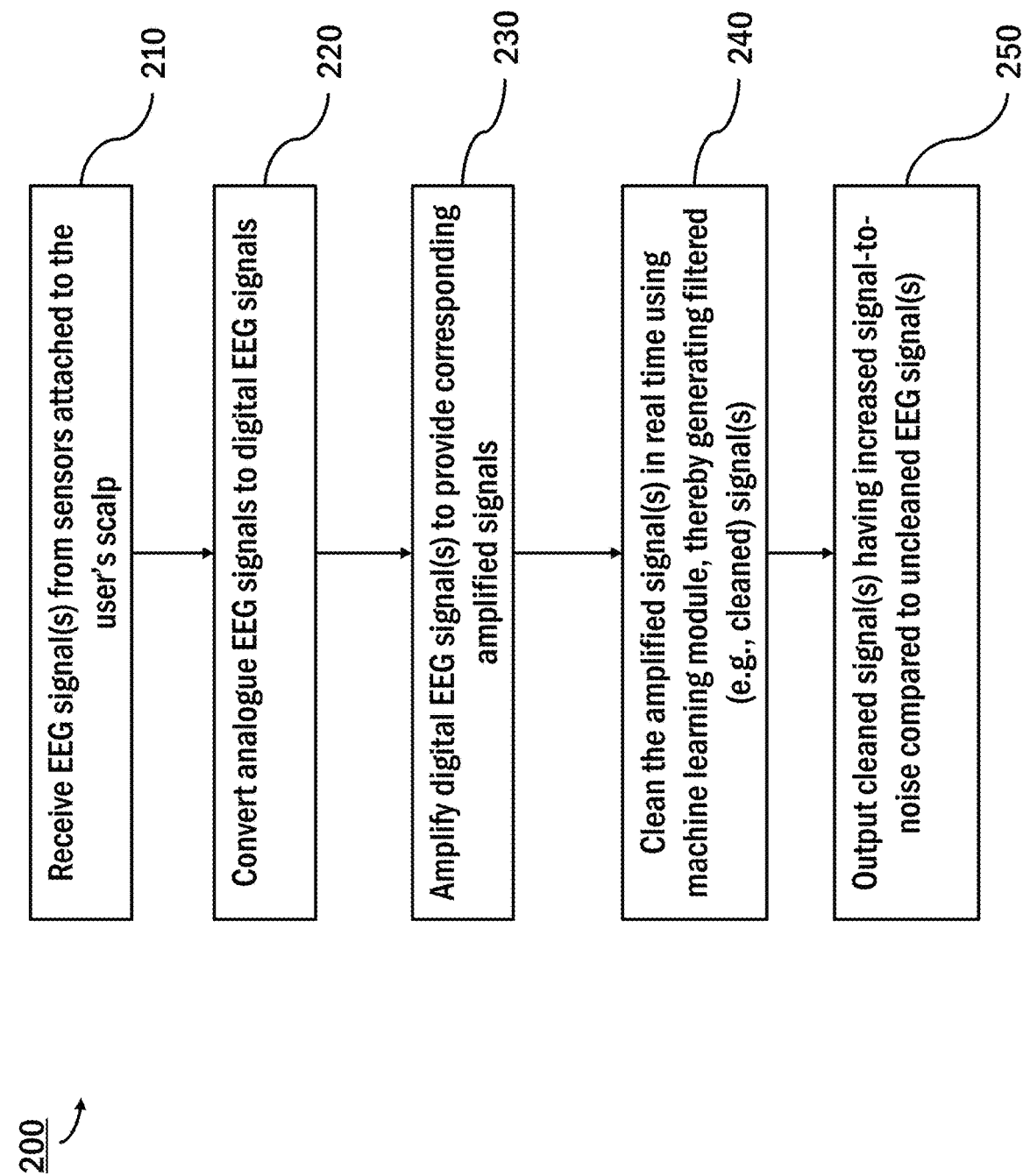
FIG. 2 is a flowchart showing aspects of the operation of the EEG system shown in FIG. 1

Referring to FIG. 2, the process of digitizing, amplifying, and cleaning an EEG signal is shown in a flowchart 200. An EEG signal, e.g., a time-varying voltage differential between a voltage measured using an active sensor and a reference sensor, is received by a bioamplifier (e.g., bioamplifier 110) from the sensors attached to the user's scalp (step 210). The frequency at which the sensor voltage is sampled should be sufficient to capture voltage variations indicative of the brain activity of interest (e.g., between 0.1 and 10 Hz, at 10 Hz or more, at 50 Hz or more, at 100 Hz or more). An ADC (e.g., ADC 112) converts the signal from an analogue signal to a digital signal (step 220) and sends the digital signal to an amplifier (e.g., amplifier 114). The digital EEG signal is then amplified (e.g., by amplifier 114) (step 230), and the amplified signal sent to a processor (e.g., processing module 120). The processor (e.g., processing module 120), in real time, cleans the amplified signal using a machine learning model (e.g., ML model 122), thereby generating a filtered (e.g., cleaned) signal (step 240), and outputs the cleaned signal having increased signal-to-noise compared to an uncleaned EEG signal (step 250).

In general, any of a variety of ML models suitable for signal processing can be used to clean the amplified EEG signal. In many cases, the ML model is a neural network, which is an ML model that employs one or more layers of nonlinear units to predict an output for a received input. Some neural networks are deep neural networks that include two or more hidden layers in addition to the input and output layers. The output of each hidden layer is used as input to another layer in the network, i.e., another hidden layer, the output layer, or both. Some layers of the neural network generate an output from a received input, while some layers do not (remain "hidden"). The network may be recurrent or feedforward. It may have a single output or an ensemble of outputs; it may be an ensemble of architectures with a single output or a single architecture with a single output.

A neural network for a machine learning model (e.g., ML model 122) can be trained on EEG-specific data in order to distinguish between actual, usable data and noise. The ML model can be trained to classify artifacts in the EEG and to deal with EEG segments that have different types of noise in different ways. For example, if the network recognizes a vertical eye movement (a blink) it could attempt to remove the blink using a different approach than it would use if it recognized a horizontal eye movement. The ML model can be trained to clean data to an arbitrary level of precision— that is, it can clean up the raw data a little bit or a lot but there is no theoretical limit as to how closely the ML model can reproduce the type of clean data it was trained on. The level of cleaning that the ML model does is dependent only on time and the architecture of the model, that is, there is no theoretical maximum amount of possible cleaning.

EEG signals, even under controlled conditions, may contain significant noise, e.g., due to biological and/or electrical sources. The propensity for noise is further increased outside of a well-controlled laboratory environment. Accordingly, ML-based noise reduction may be particularly beneficial in providing usable EEG data in real time in real world (i.e., outside of a well-controlled environment) conditions.

As noted previously, a processor (e.g., processing module 120) includes a machine learning two-choice decision model (e.g., ML two-choice decision model 124) for analyzing cleaned EEG signals that output from a machine learning cleaning model (e.g., ML cleaning model 122). The two-choice model interprets a response of a user (e.g., user 101) to information (e.g., information 142) presented via a computer (e.g., computer 140). A user's response may be a selection of one choice among a finite set, e.g., two or more, of choices presented to the user. The two-choice model associates one of two binaries with information (e.g., information 142), such as interest (e.g., acceptance of an option) of the user in the information, or disinterest (e.g., rejection of an option).

Figure 3:
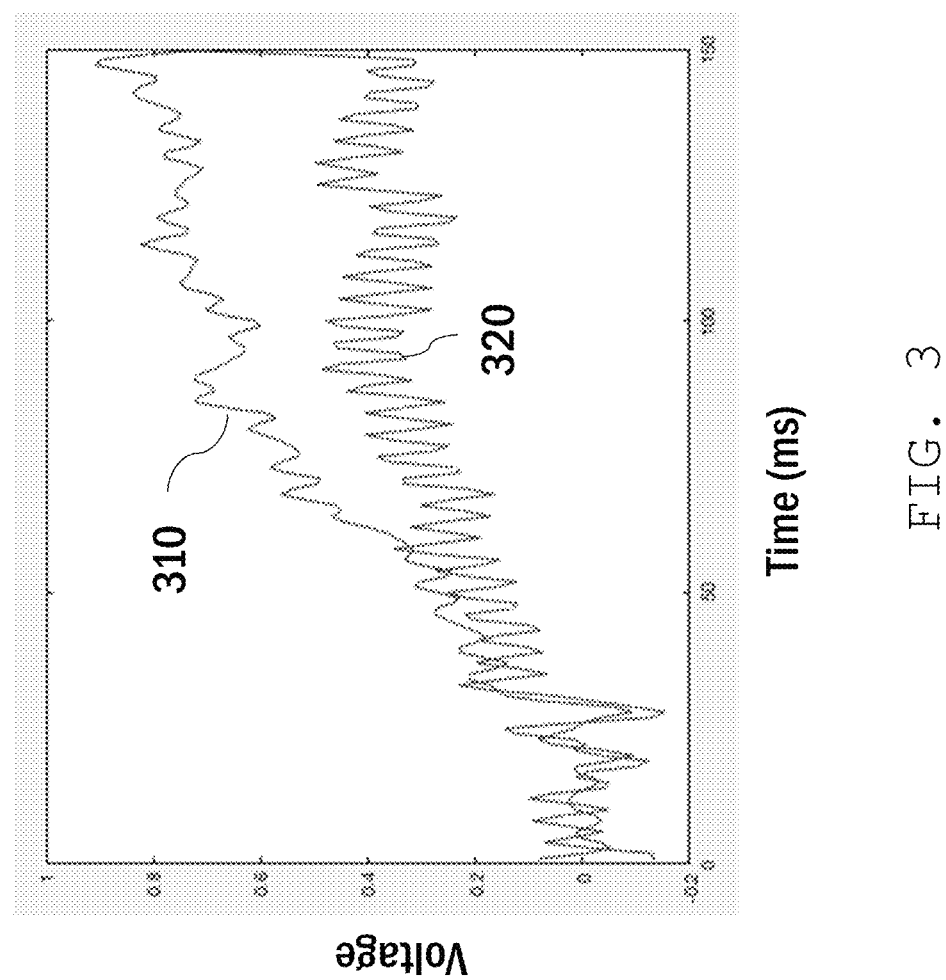
FIG. 3 is a plot comparing two EEG signals for analysis using the system in FIG. 1.

In general, various parameters of the cleaned EEG signal can be used to determine the user's response (e.g., the user's choice selection). Often, these parameters include the amplitude of the response amplitude over a relevant time period (e.g., within about 500 ms of being presented with information 142). This is illustrated in the plot shown in FIG. 3, for example, which compares two EEG signals corresponding to interest (trace 310) and disinterest (trace 320) in information presented to the user. After an initial latency of approximately 50 ms, trace 310 has a significantly larger amplitude than trace 320. A machine learning model (e.g., ML model 124) associates the higher amplitude with the user's interest, and returns this information to a computer (e.g., computer 140).

Figure 4:
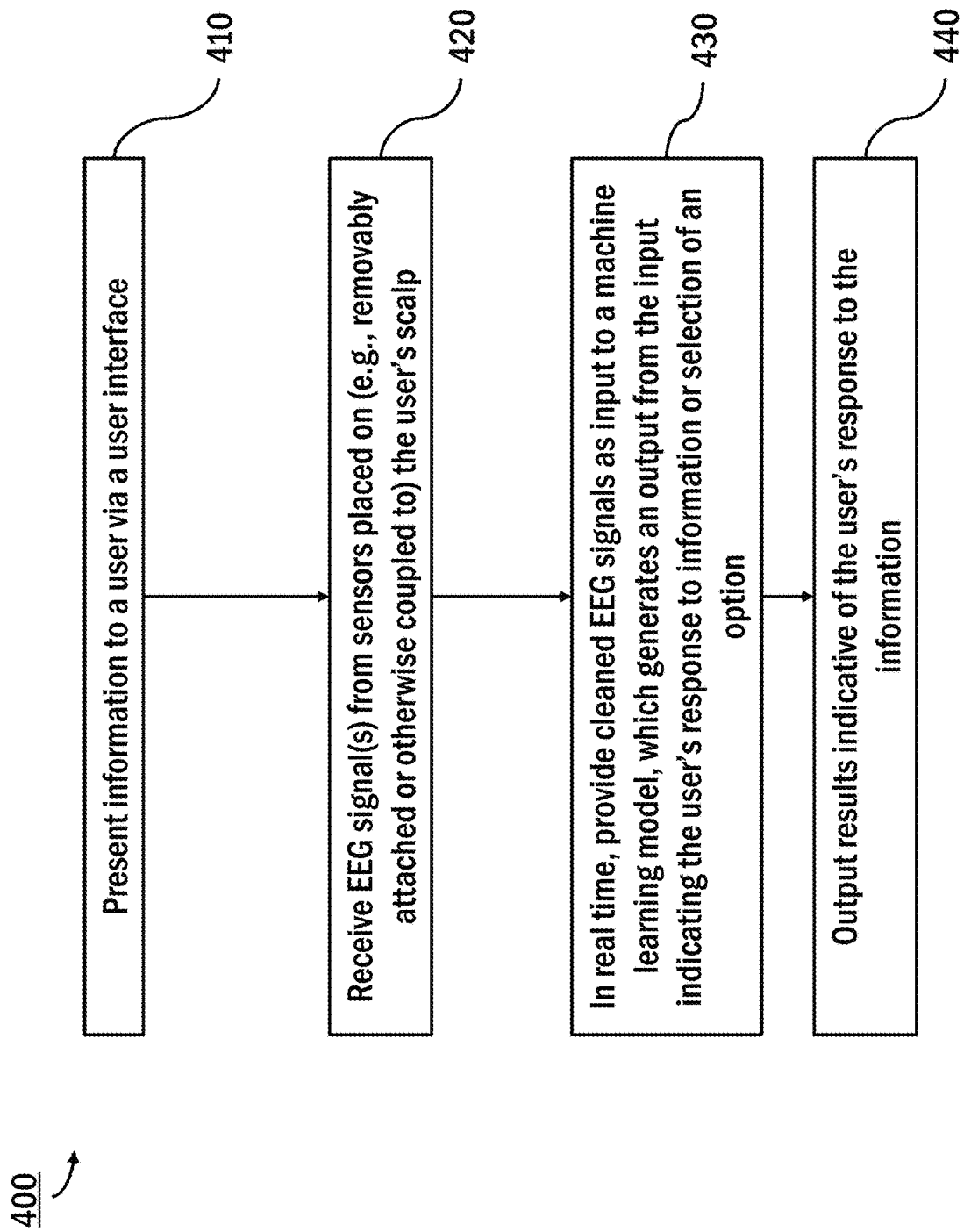
FIG. 4 is a flowchart showing other aspects of the operation of the EEG system shown in FIG. 1.

This process is illustrated by flowchart 400 shown in FIG. 4. In step 410, a system (e.g., system 100) presents information (e.g., information 142) to a user (e.g., user 101) via a user interface, for example, provided by a personal computer (e.g., personal computer 140). The system (e.g., system 100) receives EEG signals from the system's sensors placed on (e.g., removably attached or otherwise coupled to) the user's scalp (step 420). The system (e.g., system 100) amplifies and cleans the signals as described above using an amplifier and a machine learning model (e.g., ML model 122). The system (e.g., system 100) then provides the cleaned EEG signals as input to a machine learning model (e.g., ML model 124), which generates an output from the input indicating the user's response to information (e.g., information 142) or selection of an option (step 430). The system provides input and generates output in real-time to feed a closed loop. In embodiments, signal analysis involves correlating the cleaned EEG signal to the presentation of information to the user (e.g., by matching a time-stamp associated with signal to the time of presentation) and observing the time-varying amplitude of the signal associated with the user's brain activity responsive to the information. The system can decompose the signal into a time series of signal amplitude and/or change in signal amplitude and perform mathematical operations on the time series to determine the user's intent. For example, the mathematical operations can associate a change in signal amplitude above a certain threshold and within a certain time (e.g., with 50 ms or less) of presenting the user with the information with a particular intention (e.g., an affirmative response) and a change in signal amplitude below the threshold with the opposite intention (e.g., a negative response). The threshold amplitude and/or response time can be determined by training the ML model.

The system (e.g., system 100) then outputs results indicative of the user's response to the information (step 440). The user's response to the information may be a selection among multiple choices. For example, the user may be presented with a menu of options to order for dinner. The user may respond with EEG signals that the system can process to determine the user's dinner choice. The system can then output the selected dinner choice of the user.

In some embodiments, a bioamplifier (e.g., bioamplifier 110) can relay the results of two-choice decision model analysis to another device (e.g., personal computer 140), which may take certain actions depending on the results. Examples are described below.

In some embodiments, the cleaning and analysis processing occurs on the same processing module (e.g., using the same processor, e.g., the same processor core), the system does not need to send the signals across a network and therefore does not incur added data processing latency of network connections or bandwidth restrictions. The system executes calculations as soon as the amplified signal is ready for processing, providing a very low lag response to the user.

Moreover, the system can operate as a closed-loop system. For example, the bioamplifier and other device (e.g., personal computer 140) operate using feedback in which the system regulates presentation of information to the user by the device based on the analysis of the user's prior or contemporaneous EEG signals. For instance, the device can present the user with a choice between two or more different options and, based on the user's selection as interpreted from the associated EEG signals, present subsequent choices to the user associated with the user's prior choice.

In some embodiments, the system (e.g., system 100) can use the received EEG signals from the user's brain activity to determine a user's selection among the finite set of possibilities and subsequently perform an action based on the user's selection without requiring the user to provide more input than the brain activity signals. In order to determine the correct action to execute, a machine learning model (e.g., ML model 124) takes EEG signals as input and classifies the EEG signals according to the user's intended action. This is achieved by processing the cleaned EEG input to the machine learning model (e.g., ML model 124) through the hidden layers of the model and performing machine classification. This may involve, for example, feature extraction or successive nonlinear recordings.

Essentially, the cleaned data is presented to the machine learning model (e.g., ML model 124) and then the machine learning model (e.g., ML model 124) performs a number of mathematical transformations of the cleaned data in order to produce an output that reflects the intention of the user as encoded in the EEG data. The ML model is able to do this because it has been extensively trained, prior to interaction with the user, on what types of EEG signals correspond to what types of responses (e.g., selections by the user).

In general, a variety of neural networks can be used to analyze and classify the data. For example, the neural network can be a convolutional neural network model, a support vector machine, or a generative adversarial model. In some implementations, lower dimensional models, e.g., a low featural multilayer perceptron or divergent autoencoder can be implemented. The minimum number of features that can be used to achieve acceptable accuracy in decoding the user's intention is preferred for computational simplicity. The optimized models may be trained or simulated in constrained computing environments in order to optimize for speed, power, or interpretability. Three primary features of optimization are 1) the number of features extracted (as described above), 2) the "depth" (number of hidden layers) of the model, and 3) whether the model implements recurrence. These features are balanced in order to achieve the highest possible accuracy while still allowing the system to operate in near real time on the embedded hardware.

In some embodiments, the machine learning model (e.g., ML model 124) uses sub-selection in which the model only compares the current user's brain activity with other user samples that are most similar to that of the user in order to determine the user's selection. Similarity to other users can be operationalized with standard techniques such as waveform convolution and normalized cross correlation. Alternatively, the machine learning model (e.g., ML model 124) compares the user's brain activity to that of all brain activity present in a large dataset. The dataset may contain brain activity samples from one or more other users. Samples for comparison are drawn either from 1) a data system's internal user data or 2) data collected from external users who have opted-in to having their data be included in the comparison database. All samples are anonymized and are non-identifiable.

To train the machine learning model (e.g., ML model 124), a system (e.g., system 100) can present a user with a choice problem, e.g., a two-choice problem, using a display on a personal computer (e.g., computer 140) or some other interaction element. In some implementations, the system (e.g., system 100) provides the user with one object at a time, e.g., for 500 milliseconds, with random jitter, e.g., between 16 and 64 milliseconds, added between objects. Each image shown to the user is either an image of a first type of object or an image of a second type of object. Prior to displaying any images, the user is told to pay particular attention to the first type of object, e.g., by counting or some other means. While the system (e.g., system 100) is presenting images to the user, it differentiates EEG signals between when the user is paying particular attention to images of the first type of object and when the user is not paying as close of attention to images of the second type of object.

For example, the system (e.g., system 100) presents the user with sequence of images showing one of two different objects (e.g., a rabbit or a squirrel). Prior to displaying images, the user is told to pay particular attention to images of squirrels only, and to count the squirrels. As each image displays, the system (e.g., system 100) records the user's brain activity and determines a difference between when the user views an image of a rabbit and when the user views an image of a squirrel. This difference is attainable because 1) the squirrels are task-relevant (to the task of counting squirrels) and the rabbits are not and 2) the squirrel-counting task requires an update of working memory (i.e., the number of squirrels that have been viewed) each time a squirrel appears. These cognitive processes are reflected in relatively large signals measurable by the EEG system and separable by the ML model.

In some embodiments, the machine learning model (e.g., ML model 124) can be trained using equal numbers of objects so that the model does not learn the true population frequency distribution of the objects in the user's world, which may impair the model's ability to distinguish between the user's choices. For example, the system may be trained with equal numbers of squirrels and rabbits, though most users encounter squirrels more often than rabbits.

After collecting samples from the user, the system (e.g., system 100) classifies the user's EEG signals to distinguish between EEG signals elicited when the user is focused on an image (e.g., views the squirrel in the example above) and when the user is not (e.g., the rabbit). This is accomplished by the machine learning model (e.g., ML model 124). Prior to being passed to the ML system, the signals may be pre-processed, such as by boxcar filtering, range-normalization, or length normalization. The pre-processed signals are then passed to the machine learning model (e.g., ML system 124) for classification. The classification may be implemented in either a single-model fashion (i.e., classification is done by a single model) or in an ensemble-model fashion (i.e., a number of different types of models all make a classification and then the overall choice is made by a vote). In some implementations, the user samples can be added to the dataset in a database accessible to the system (e.g., system 100) and used to train subsequent neural network models.

Once the model is trained broadly across multiple functional objects, tasks, and people, the system can use the ML model on any person for any decision task without further training. The more similar the new decision task is to the trained task, the more effective this transfer will be.

ML models can be trained on various characteristics of the user. For example, in some implementations, models may be trained on a specific age group, e.g., over 40 or under 20. The model may take into account a user's age and choose user samples in the same age range or choose from a subset of user samples in the database. As described above, the database will consist of both internal data and data from external users who have opted-in to their data being included in the comparison database. All samples are anonymized and non-identifiable. Individuals will have the option to include not only their EEG data, but other demographic data such as age and gender. System 100 can then use the trained model in real-life scenarios to distinguish between a selection event by the user and rejection.

In general, an EEG system (e.g., EEG system 100) can present a user (e.g., user 101) with choices among a finite set, e.g., two or more, of possibilities, determine the choice that the user (e.g., user 101) has made based on EEG signals from brain activity, and then perform further actions based on the user's choice. As a result, the user (e.g., user 101) can cause the system (e.g., system 100) to perform certain actions without any physical action beyond having the user view the choices on a display and generate brain activity from a selection of the viewed choices.

For example, the user (e.g., user 101) can choose a contact from a list of multiple contacts and place a phone call the chosen contact using only the user's brain activity. To perform this activity, the EEG system (e.g., EEG system 100) sequentially presents the user (e.g., user 101) with a list of contacts via a computer (e.g., computer 140) and identifies a selection from the list based on received EEG signals from the user's corresponding brain activity. Next, the system (e.g., system 100) presents the user (e.g., user 101) with options for contacting the selected contact, e.g., call, text, share, or email. Again, the system identifies the user's selection based on received EEG signals corresponding to the user's brain activity representing a selection of an option. The system (e.g., system 100) then performs the call or provides instructions to a telephone to make the call.

Figure 5:
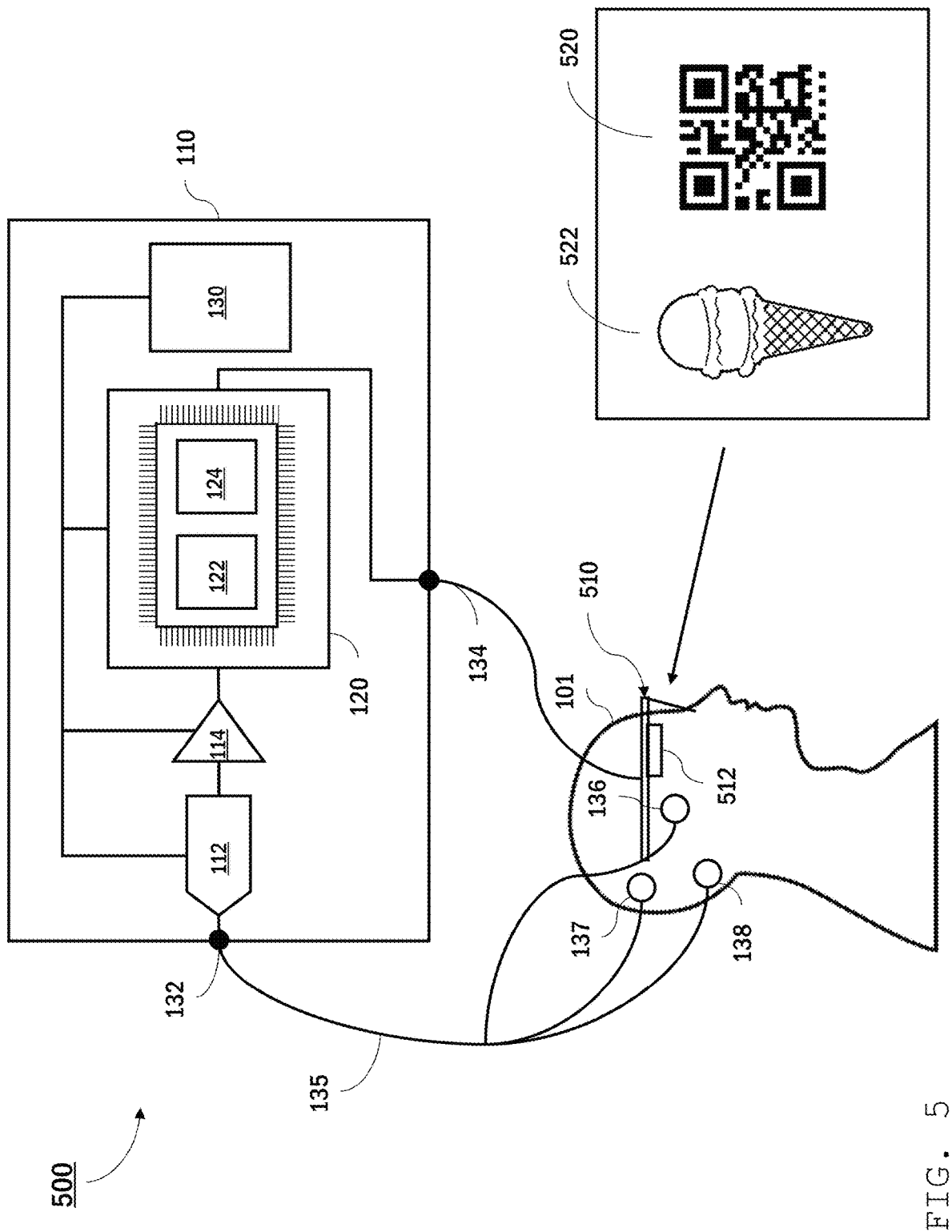
FIG. 5 is a schematic diagram of an embodiment of an EEG system that features a head-mounted camera.

While bioamplifier 110 is interfaced with personal computer 140 in system 100, other configurations are also possible. Referring to FIG. 5, for example, an EEG system 500 includes bioamplifier 110 interfaced with a head-mounted camera system 510 which is arranged to track user 101's field of view. Camera system 510 includes a camera 512 and onboard image processing for analyzing images captured by the camera of user 101's field of view. For example, EEG system 500 is configured to facilitate user 101's interaction with an object 522 associated with a quick response (QR) code 520 (as illustrated) or bar codes, NFC tags, or some other identification feature readily identifiable using machine vision.

An EEG system (e.g., system 500) analyzes EEG signals from a user (e.g., user 101) associated with brain waves responsive to a viewing object (e.g., viewing object 522) synchronously with reading a QR code (e.g., QR code 520). The analysis returns one of two binary choices, which the system associates with the viewing object (e.g., object 522) based on the system viewing the QR code (e.g., QR code 520).

Figure 6:
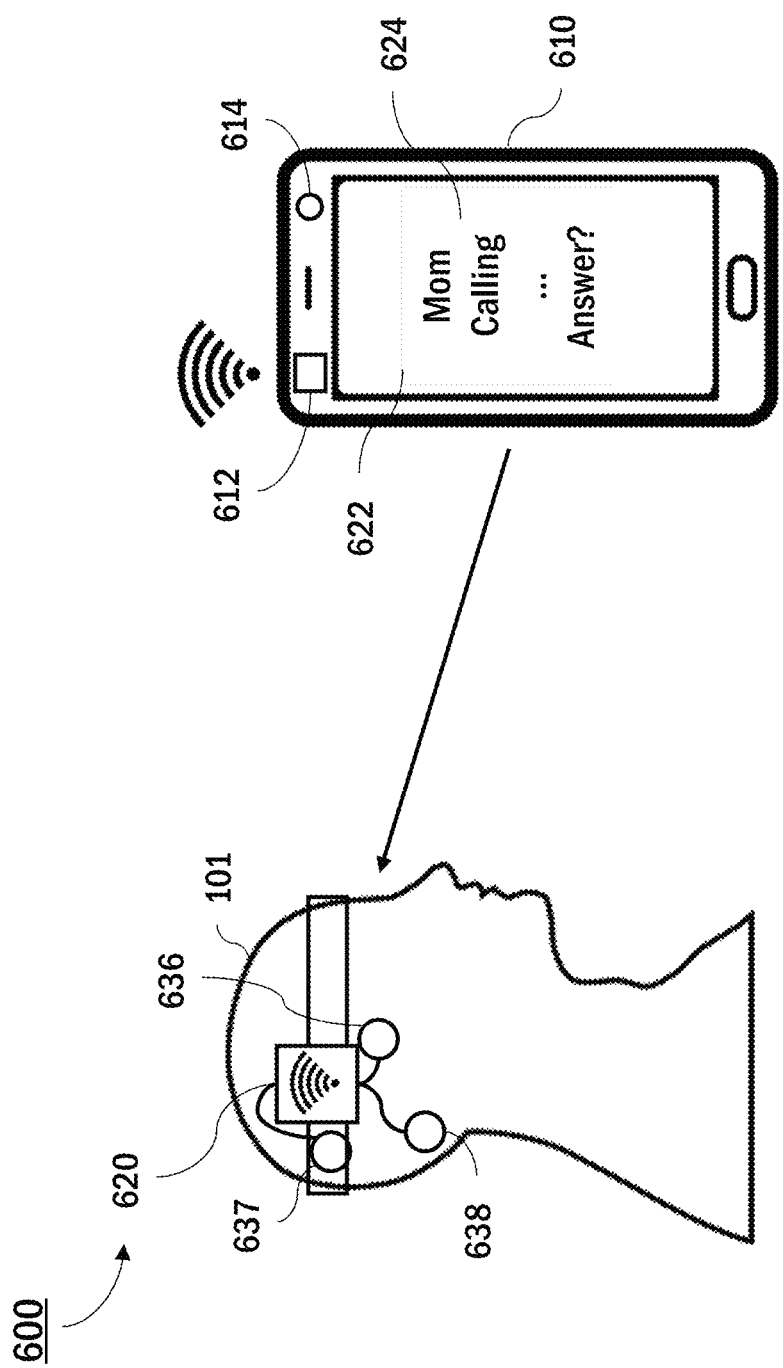
FIG. 6 is a schematic diagram of another embodiment of an EEG system that features a mobile phone and a wireless connection to the system's sensor electrodes.

While the systems described above both feature a portable bioamplifier (i.e., bioamplifier 110), that connects with either a computer or other interface, other implementations are also possible. For example, the components of a bioamplifier (e.g., bioamplifier 110) can be integrated into another device, such as a mobile phone or tablet computer. Moreover, while the foregoing systems includes sensors that are connected to the portable bioamplifier using leads, other connections, e.g., wireless connections, are also possible. Referring to FIG. 6, for instance, an EEG system 600 includes a mobile phone 610 and a head-mounted sensor system 620. The cleaning and analysis functions of the components of portable bioamplifier 110, personal computer 140, and/or camera system 510 described above are all performed by mobile phone 610 alone, or in conjunction with cloud-based computer processors. Mobile phone 610 includes a wireless transceiver 612, a display 622, and a camera 614.

Sensor system 610 includes a transceiver unit 620 and sensors 636, 637, and 638 connected to the transceiver unit. The sensors measure EEG signals as described above, but the signals are related to receiver 612 using a wireless signal transmission protocol, e.g., BlueTooth, near-field communication (NFC), or some other short-distance protocol.

During operation, a mobile phone (e.g., mobile phone 610) displays information (e.g., information 624) to a user (e.g., user 101) on a display (e.g., display 622) and, synchronously, receives and analyzes EEG signals from a transceiver unit (e.g., transceiver unit 620). Based on the EEG signal analysis, the mobile phone (e.g., mobile phone 610) can take certain actions related to the displayed information. For instance, the phone can accept or reject phone calls based on the EEG signals, or take some other action.

Alternatively, or additionally, a user (e.g., user 101) can use a camera (e.g., camera 614) to capture information in their environment (e.g., to scan a QR code) while the phone receives and analyzes their associated brain waves.

In general, the EEG systems described above can use a variety of different sensors to obtain the EEG signals. In some implementations, the sensor electrodes are "dry" sensor which feature one or more electrodes that directly contact the user's scalp without a conductive gel. Dry sensors can be desirable because they are simpler to attach and their removal does not involve the need to clean up excess gel. A sensor generally includes one or more electrodes for contacting the user's scalp.

Referring to FIGS. 7A-7D, for example, a sensor 700 includes multiple wire loop electrodes 720 mounted on a base 710, and a press stud electrode 730 on the opposite side of base 710 from loops electrodes 710. Wire loop electrodes 720 are bare electrically-conducting wires that are in electrical contact with metal press stud 730. During use, a user can position sensor 700 in their hair with the top of wire loop electrodes contacting their scalp. A lead, featuring female press stud fastener, is connected to press stud 730, connecting sensor 700 to a bioamplifier or transceiver. The multiple loop electrodes provide redundant contact points with the user's scalp, increasing the likelihood that the sensor maintains good electrical contact with the user's scalp.

As is apparent in FIG. 7C (top view), sensor electrode 700 includes a total of eight wire loop electrodes arranged symmetrically about an axis. More generally, the number of wire loop electrodes can vary as desired. The length of the wire loop electrodes (from base to tip) can also vary as desired. For instance, a user with long hair may select a sensor with longer wire loops than a user with shorter hair. FIG. 8, for example, shows another sensor electrode 800 similar to sensor electrode 700 but with shorter wire loop electrodes 820. In general, the loop electrodes can have a length from about 1 mm to about 15 mm.

FIG. 9 shows yet a further sensor electrode 900 that includes multiple wire electrodes 920. Wire electrodes 920 can be sufficiently flexible so that the user can bend them to provide optimal contact with the scalp. Each wire electrode 920 can have the same length, or the lengths of the wires can vary.

Figure 10A:
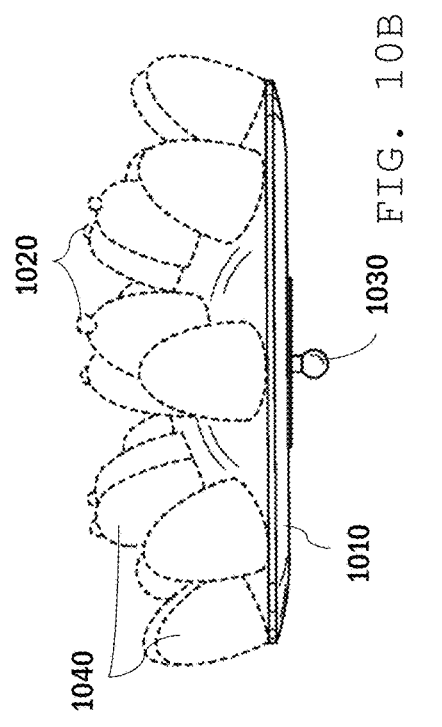
FIG. 10A is a perspective view of an embodiment of a sensor electrode that includes multiple protuberances.
Figure 10B:
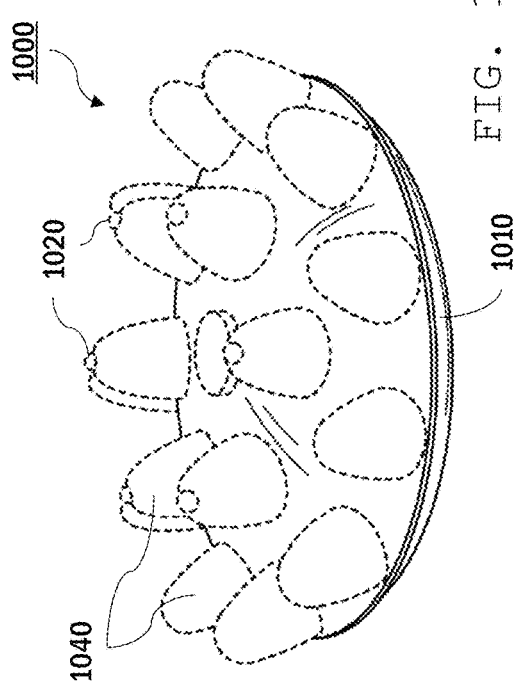
FIG. 10B is a side view of the sensor electrode shown in FIG. 10A.
Figure 10D:
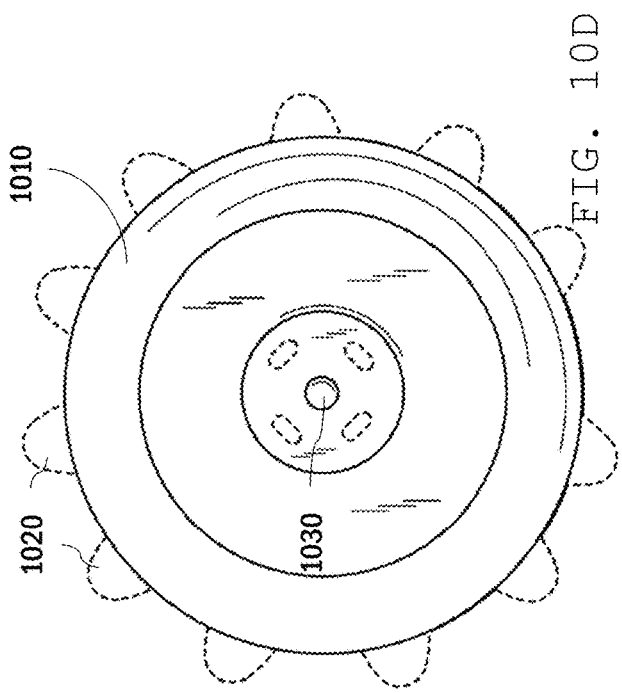
FIG. 10D is a bottom view of the sensor electrode shown in FIG. 10A.
Figure 10C:
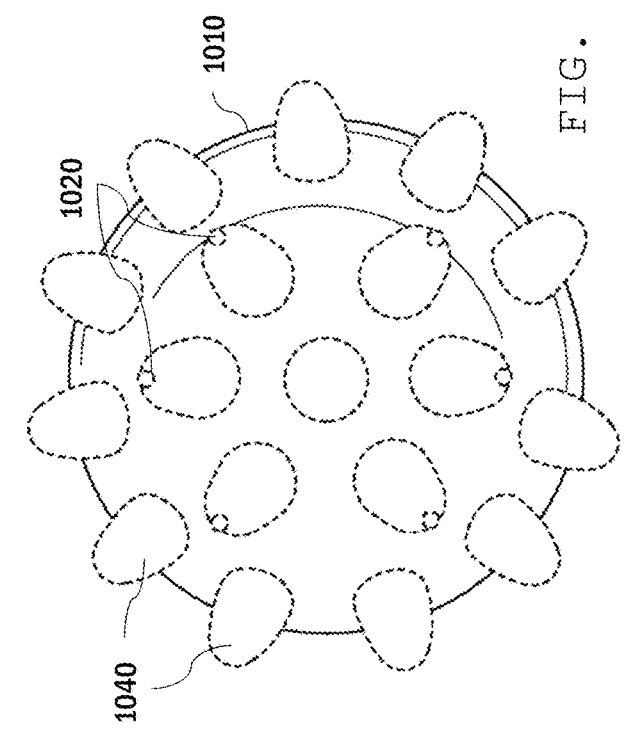
FIG. 10C is a top view of the sensor electrode shown in FIG. 10A.

Other dry sensor designs are also possible. For example, referring to FIGS. 10A-10D, a sensor electrode 1000 features multiple protuberances 1040 supported by a base 1010. The protuberances are formed from a relatively soft material, such as a rubber. As seen from a top view, as shown in FIG. 10C, protuberances 1040 are arranged in two concentric rings. The protuberances in the inner ring each include a wire electrode 1020 which protrudes from the tip of the respective protuberance. The protruding wire electrodes can be relatively short, reducing possible user discomfort due to the excessive pressure on the user's scalp.

Referring to FIGS. 11A-11E, a further example of a sensor electrode 1100 includes a base 1110, wire electrodes 1120, a press stud electrode 1130, and a protective cap 1140 (e.g., a plastic cap). The cap can reduce the likelihood that the user's hair becomes ensnared in the electrode, e.g., where the electrodes are attached to the base.

In certain embodiments, consistent, good electrical contact between an EEG sensor and the user's scalp can be achieved by using a sensor device that grips locks of the user's hair and then ratchets, rolls, or motors up, using a power actuator, the hair to anchor the sensor against the user's scalp. The sensor device features a mechanical mechanism that grips the user's hair and easily allows movement in one direction, but does not allow easy movement in the other direction so that the sensor device consistently moves forward towards the user's scalp.

Figure 12:
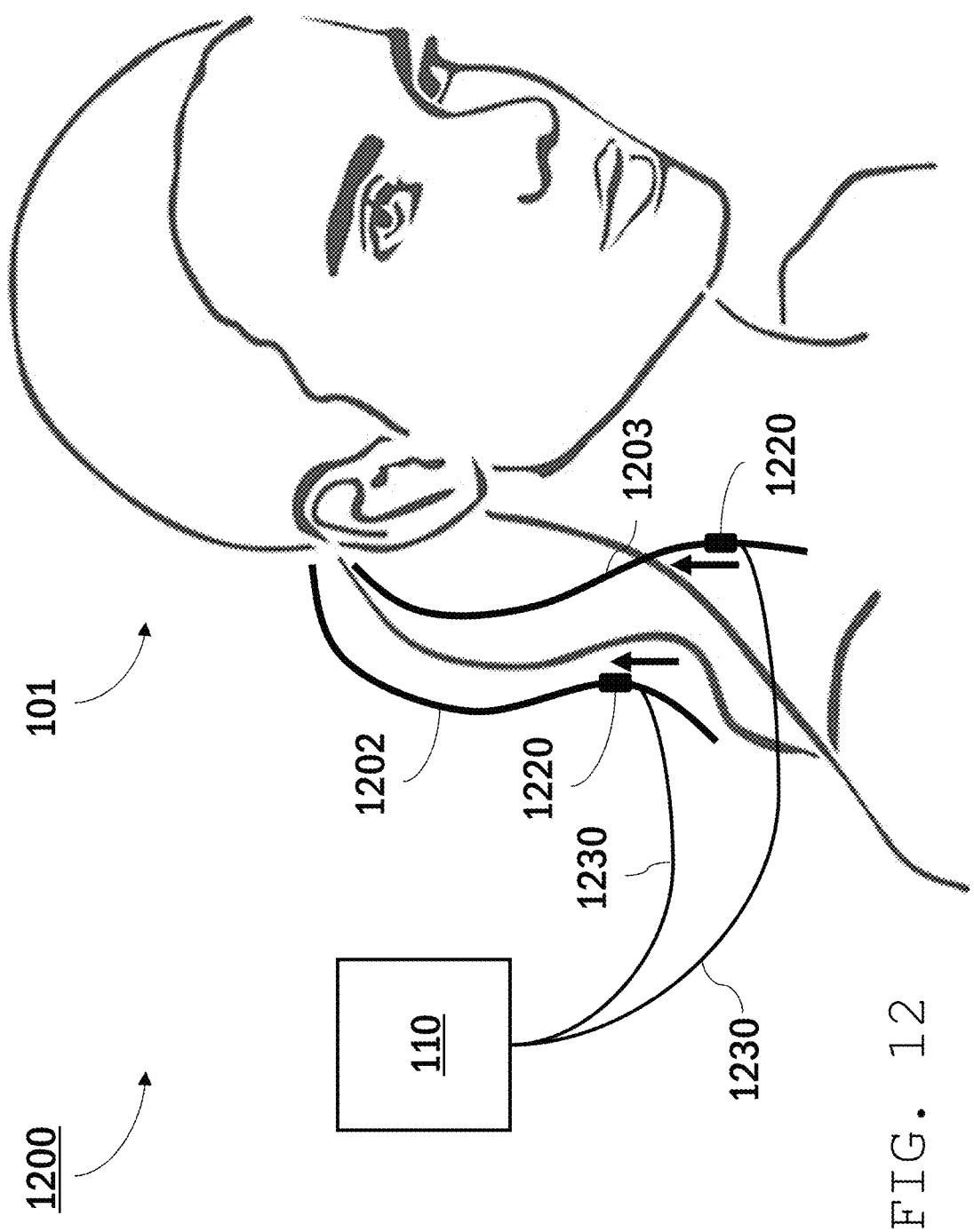
FIG. 12 is a schematic diagram illustrating use of an EEG system using hair ratcheting sensors.

Referring to FIG. 12, an EEG system 1200 features sensor devices 1220 that each grip a lock of hair 1202, 1203 of user 101, which the user then moves along the hair lock to the user's scalp. Devices 1220 each include a device (e.g., a ratcheting device) that permits easy movement along the hair lock towards the scalp, but prevents easy movement in the opposite direction so that the devices maintain good contact with the user's scalp once applied. The sensor devices are attached to leads 1230 that connect to bioamplifier 110, facilitating signal transmission between devices 1220 and bioamplifier 110.

Generally, hair ratcheting sensor devices use a mechanical approach, e.g., threading, snapping, or clipping, to grip locks of the user's hair. The hair ratcheting sensor devices 1220 each contain a channel through which locks of user's hair 102, 103 is threaded in one direction. Any number of mechanical insertion approaches can be viable in order for the sensor device to grip locks of the user's hair 102, 103. For example, the sensor device may include an adjustable clamp, e.g., similar to adjustable clamps commonly used to clamp objects to a line of thread.

Generally, sensors 1220 include a mechanism for moving the sensor preferentially in one direction, towards the user's scalp. In some embodiments, this mechanism is a ratchet, which is a mechanical device that allows continuous linear or rotary motion in only one direction while preventing motion in the opposite direction. Generally, linear or rotary ratchets can be used. For example, referring to FIGS. 13A-13C, a sensor 1320 is composed of a sensor housing 1325 (e.g., a metal and/or plastic element that contains other components of the sensor) and a series of electrode pins 1340. A channel 1326, through which the user threads a lock of their hair, runs through housing 1325. A lead 1330 connects sensor 1320 to the bioamplifier. Each of electrode pin 1340 is in parallel electrical communication with lead 1330, as illustrated by the dotted connections in FIG. 13B.

A ratchet is arranged within channel 1326 and arranged to allow easy movement of sensor 1320 along a lock of hair in the +z direction, but inhibits movement in the −z direction. The ratchet is composed of two interlocking layers, locking layer 1350 and layer 1355. Locking layer 1350 includes a base 1351 and a series of pawls 1353 each attached to layer 1351 by a corresponding springing hinge 1352. The springing hinges allow rotation of the corresponding pawl towards base 1351 upon application of a force, but restore the pawl to its resting position when the force terminates.

Layer 1355 includes a base 1356 that supports a linear rack of teeth 1353 which interlock with pawls 1353 when the pawls are in their resting positions. Teeth 1353 are uniform but asymmetrical, with each tooth having a moderate slope on one edge and a much steeper slope on the other edge.

When a lock of hair threaded is through channel 1326 and the sensor is moved in the unrestricted (i.e., +z) direction, the pawls rotate upwards towards base 1351, opening the channel and allowing easy movement of the sensor along the hair. When the sensor is moved in the opposite direction, the pawls relax to engage teeth 1353 with the lock of hair between them, making motion of the sensor along the hair lock in the −z direction difficult or impossible.

Sensor 1320 also includes a hinge 1322 which runs along the length of housing 1325, and a magnetic lock 1328 (see FIG. 13B). To release sensor 1320 from the lock of hair, the user releases magnetic lock 1328 (e.g., by prying the two parts of the lock apart) and opens the sensor about hinge 1322. This opens up channel 1326, releasing interlocking layers 1350 and 1355, allowing the user to remove the sensor from their hair with ease. FIG. 13B illustrates the sensor with the channel opened.

Figure 14:
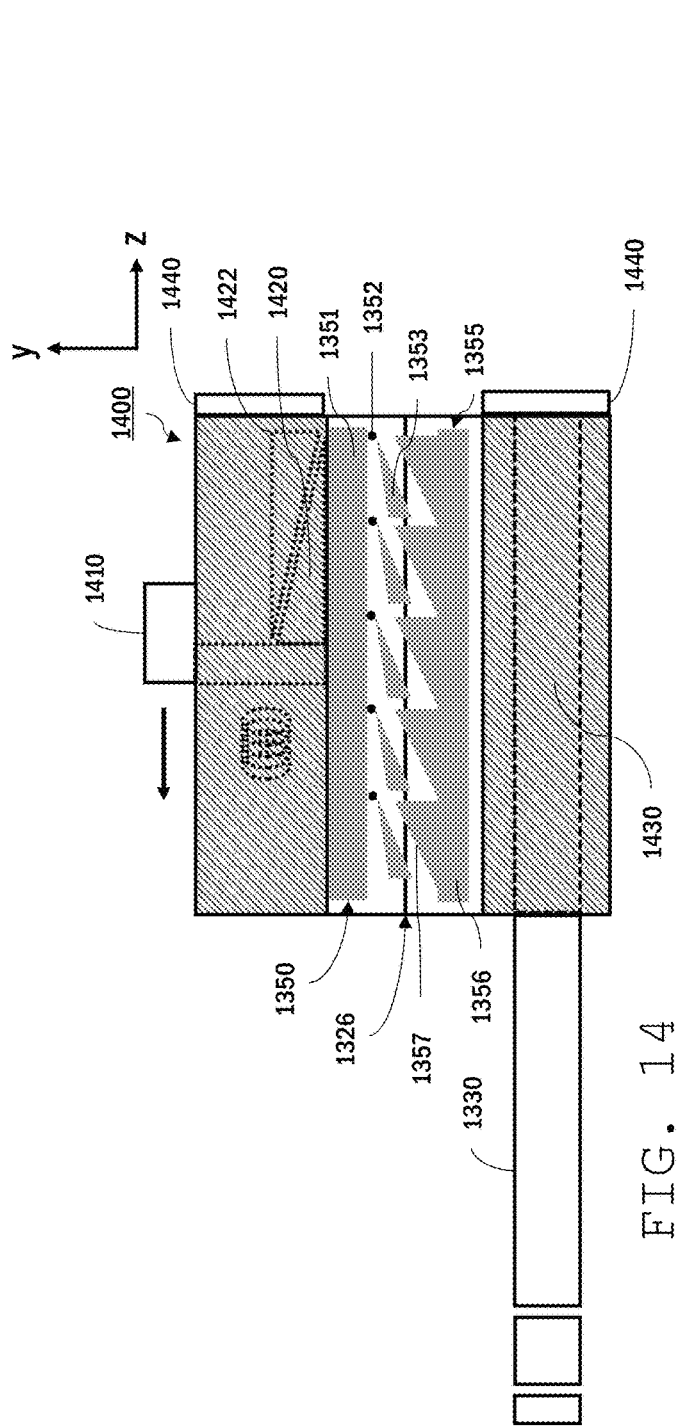
FIG. 14 is a cross-sectional view of another embodiment of a hair ratcheting sensor.

While sensor 1320 features a fastener (i.e., magnetic fastener 1328) and hinge mechanism (i.e., hinge 1322) to allow the user to release the sensor, other implementations are possible. For example, referring to FIG. 14, a sensor device 1400 includes a release latch 1410 for disengaging pawls 1353 from teeth 1357, opening channel 1326 and allowing the user to thread device 1300 along their lock of hair away from their scalp.

Furthermore, while sensor 1320 features six pin electrodes 1340, other arrangements are possible. For instance, sensor 1400 includes a single continuous electrode 1440 (e.g., a metalized surface of the sensor housing). Lead 1330 requires only a single point of connection 1430 to electrode 1440.

Figure 15:
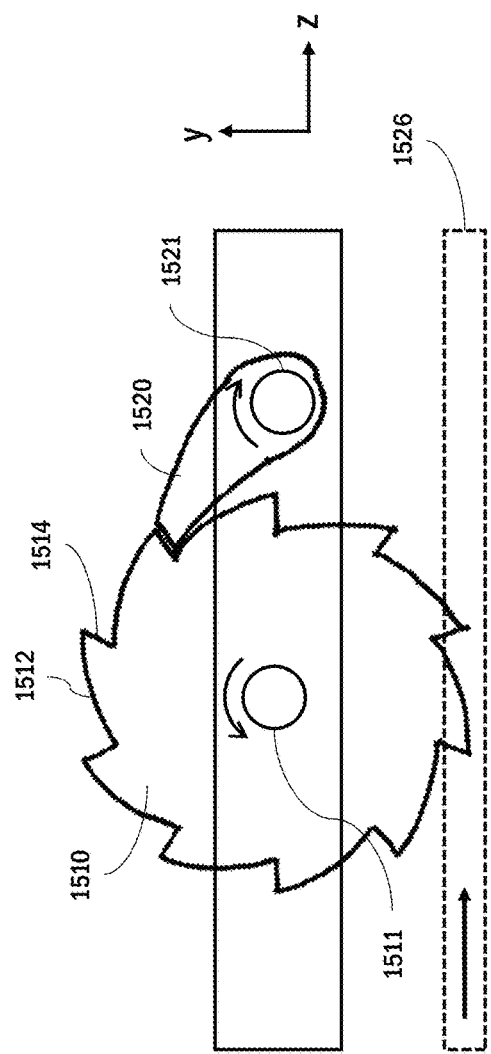
FIG. 15 is a cross-sectional view of a ratchet device for a hair ratcheting sensor.

While sensors 1300 and 1400 both feature linear ratchets, rotary ratchets are also possible. For example, referring to FIG. 15, in some embodiments, sensor devices include a ratchet composed of a gear 1510 and a pawl 1520, but attached to a frame via corresponding axles 1511 and 1521, respectively. Gear 1510 includes teeth that each feature a gently sloping surface 1512 and a steep surface 1514. Anticlockwise motion of gear 1510 cause pawl to ride along surface 1512 of the adjacent tooth, rotating clockwise as it approaches the tooth's apex. As the pawl crests the apex, a spring mechanism built into axle 1521 causes the pawl to snap down to the gently sloping surface 1521 of the next gear tooth. Conversely, clockwise rotation of gear 1510 causes the pawl to engage the steep surface 1514 of the adjacent tooth, locking the gear and preventing rotation.

Accordingly, for a lock of hair threaded through a channel 1526 running tangential to gear 1510, motion of the hair against gear 1510 in the +z direction forces anticlockwise gear rotation which the ratchet freely permits. Movement of the hair in the opposite direction, however, requires clockwise rotation of the gear, which the pawl prevents.

In some embodiments, the sensor device release mechanism is purely mechanical (e.g., as for sensors 1300 and 1400). For example, a user may squeeze the side of the sensor body to open the sensor device hinge in order to release hair and therefore the sensor. In other embodiments, the sensor device can be released using signals from the bioamplifier regarding when to open and close the channel of the angle ratcheting structure. Signals may open the channel to allow hair to move upward towards the scalp at defined intervals or until the sensor device senses the user's scalp. The sensor device release mechanism may then stay closed until a signal from the bioamplifier either causes the hinge to open or the teeth to release.

Furthermore, while the foregoing examples of hair ratcheting sensors use mechanical ratchets, other implementations are also possible. For example, in some embodiments, sensors can use electromechanical actuators which automatically move the sensor back and forth along a lock of the user's hair.

Figure 16:
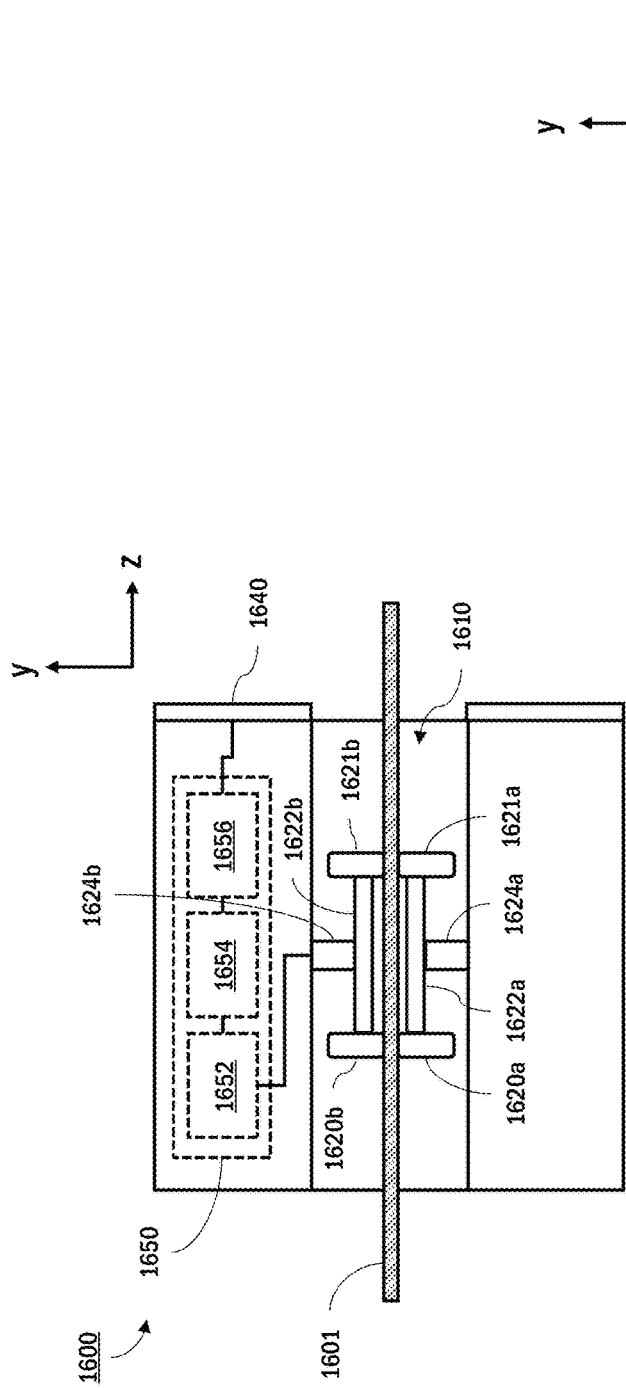
FIG. 16 is a schematic diagram of an embodiment of a hair ratcheting sensor that includes an electromechanical actuator.

Referring to FIG. 16, for example, a sensor 1600 includes an inch-worm piezoelectric actuator to move sensor 1600 along a lock of hair 1601. The inch-work actuator is mounted within a channel 1610 running through the body of the sensor and is composed of two components which pinch hair lock 1601 between them. Each component features three piezo-actuators 1620*a, b*, 1621*a, b*, and 1622*a, b*. Piezo-actuators 1620*a*, 1620*b*, 1621*a*, and 1622*b* expand/contract in the y-direction, while piezo-actuators 1622*a* and 1622*b* expand and contract in the z-direction. The piezo-actuators are attached to the sensor body via mounting attachments 1624*a* and 1624*b*, respectively.

A controller 1650 electrifies the piezo-actuators in sequence to move sensor 1600 along hair lock 1601 in the +z or −z direction as follows. Motion of the sensor is due to the lateral extension of piezo-actuators 1622*a, b* pushing on two clutching piezo-actuators 1620*a, b* or 1621*a, b*.

The actuation process of the inch-worm actuator is a six step cyclical process after the initial relaxation and initialization phase. Initially, all three piezo actuators of each component are relaxed and unextended. To initialize the inch-worm actuator the clutching piezo-actuators furthest from the direction of desired motion, e.g., piezo-actuators 1620*a, b* for motion in the +z direction are electrified first, extending these actuators to grip lock 1601 between them, then the six step cycle begins as follows: First, the lateral piezo-actuators 1622*a, b* are both extended, advancing sensor 1600 in the +z direction. Then, piezo-actuators 1621*a, b* are electrified to cause these actuators to grip lock 1601, while clutching actuators 1620*a, b* both release the lock. Lateral piezo-actuators 1622*a, b* then relax, further advancing sensor 1600 in the +z direction. Clutching piezo-actuators 1621*a, b* the release lock 1601 while 1620*a, b* grip, and the process is repeated.

Electrification of the piezo-actuators can accomplished by applying a high bias voltage to the actuators via controller 1650. To move long distances the sequence of steps is repeated many times in rapid succession. Once the motor has moved sufficiently close to the desired final position, the motor may be switched to an optional fine positioning mode. In this mode, the clutches receive constant voltage (one high and the other low), and the lateral piezo voltage is then adjusted to an intermediate value, under continuous feedback control, to obtain the desired final position.

In some implementations, positioning of sensor 1600 is controlled via a feedback control circuit to maintain a desired level of contact with the user's scalp. For example, controller 1650 includes a sensor 1656 (e.g., a contact pressure sensor or an electrical impedance sensor) which measures a parameter indicative of the degree of contact of electrode 1640 with the user's scalp. Via a processor 1654, controller 1650 monitors signals from sensor 1656 and delivers drive signals to the inch-worm actuator via a signal generator 1652. Typically, controller 1650 is provided with a threshold value or a range of values for the parameter measured by sensor 1656 and the controller operates using feedback from the sensor to adjust the sensors position using the inch-worm actuator.

While the components of controller 1650 are depicted in FIG. 16 as being contained within the body of sensor 1600, more generally, one or more of the components can be external to the sensor body, e.g., part of the bioamplifier.

Figure 17:
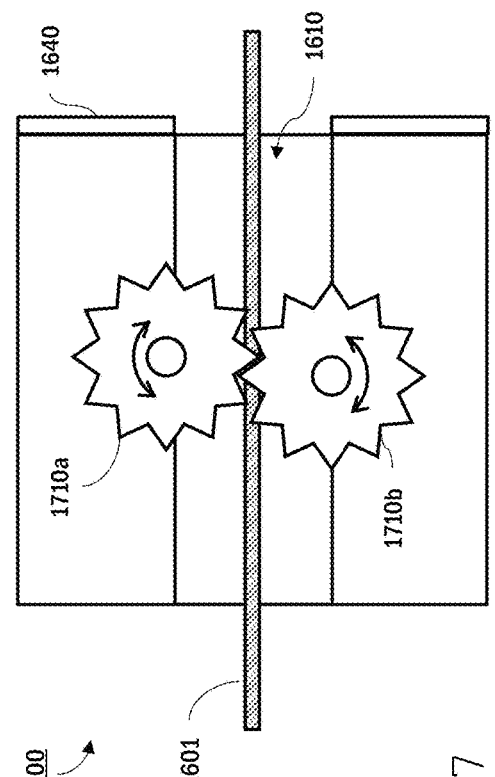
FIG. 17 is a schematic diagram of another embodiment of a hair ratcheting sensor that includes an electromechanical actuator.

Other electromechanical actuators can be used. For example, referring to FIG. 17, rotary actuators can be used. Specifically, a sensor device 1700 includes a pair of electric motors that turn two interlocking gears 1710*a* and 1710*b*. Lock 1601 is threaded between gears 1710*a* and 1710*b*, and rotation of the gears causes sensor device 1700 to advance along lock 1601 in either the +z or −z directions.

In general, the EEG systems described above can be used to accomplish a variety of computer-based tasks. For example, the disclosed system and techniques can be used to perform tasks commonly performed using a networked computer device (e.g., a mobile phone), such as ordering food, scheduling a flight, interacting with household or personal electronic devices, and/or purchasing a ticket for an event. The system can be used for user interaction with objects that have QR codes, bar codes, NFC tags, or another type of identification feature on them so that a system can detect the object with which the user is interacting and determine tasks associated with the object. These can be objects in a user's home such as a thermostat, television, phone, oven, or other electronic device. By way of example, an automated pet door in the user's house may have an associated QR code. By receiving the QR code from the dog door, the system may determine that the user is interacting with the door with their mobile phone. The system then can present the user with a list of options associated with the pet door on their phone. The system can then collect and analyze the user's EEG signals to determine what action the user would like the system to perform, in this example, whether or not to lock the pet door. Similarly, a system (e.g., EEG system 100) may use a user's phone or other computing device to notice proximity of a smart device. Proximity can be recognized by wireless or wired connectivity, (e.g., Bluetooth, near field communication, RFID, or GPS). Once proximity is determined, the system can present the user with a choice related the smart device. For example, a user's phone may be able to notice that it is in proximity to a smart thermostat, such as a Nest, a Honeywell Lyric Round, or a Netatmo's thermostat, and then present the user with a choice about whether the user would like the temperature to be warmer or colder. Using the EEG decision making protocol described above, the system could then adjust the temperature in the room on the basis of the user's EEG, without the user having to physically interact with the thermostat. Any other two choice decision that can be made for a smart device (e.g., a smart home device such as an Amazon Alexa, Google Home, or Wemo plug device) could be implemented in the same way—for example turning a smart light on or off, turning the volume of a smart speaker up or down, or making a decision to buy or not to buy what is in a digital shopping cart.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively, or in addition, the program instructions can be encoded on an artificially-generated propagated signal, e.g., a machine-generated electrical, optical, or electromagnetic signal, which is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

Figure 18:
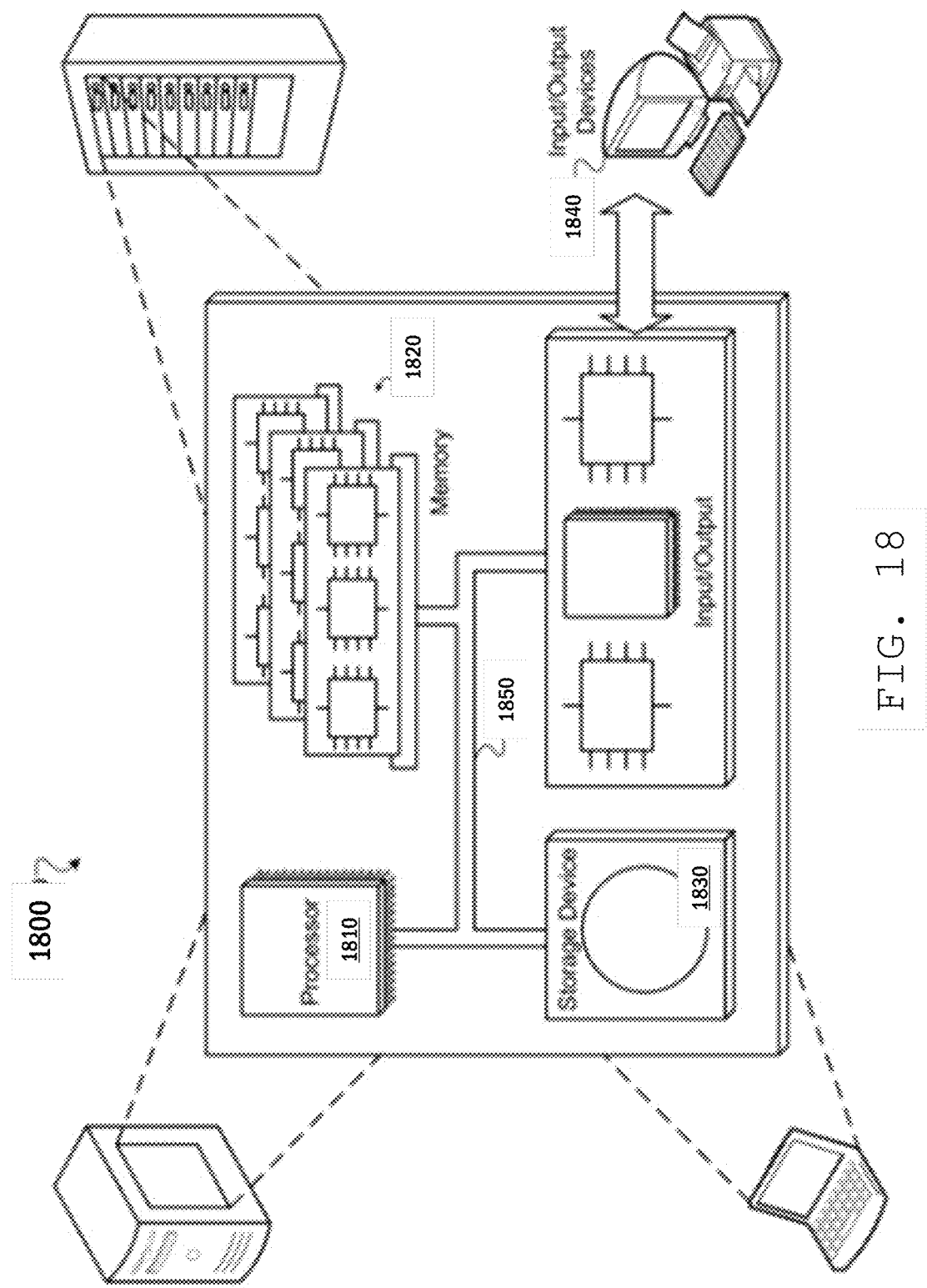
FIG. 18 is a schematic diagram of a data processing apparatus that can be incorporated into an EEG system.

An example of one such type of computer is shown in FIG. 18, which shows a schematic diagram of a generic computer system 1800. The system 1800 can be used for the operations described in association with any of the computer-implemented methods described previously, according to one implementation. The system 1800 includes a processor 1810, a memory 1820, a storage device 1830, and an input/output device 1840. Each of the components 1810, 1820, 1830, and 1840 are interconnected using a system bus 1850. The processor 1810 is capable of processing instructions for execution within the system 1800. In one implementation, the processor 1810 is a single-threaded processor. In another implementation, the processor 1810 is a multi-threaded processor. The processor 1810 is capable of processing instructions stored in the memory 1820 or on the storage device 1830 to display graphical information for a user interface on the input/output device 1840.

The memory 1820 stores information within the system 1800. In one implementation, the memory 1820 is a computer-readable medium. In one implementation, the memory 1820 is a volatile memory unit. In another implementation, the memory 1820 is a non-volatile memory unit.

The storage device 1830 is capable of providing mass storage for the system 1800. In one implementation, the storage device 1830 is a computer-readable medium. In various different implementations, the storage device 1830 may be a floppy disk device, a hard disk device, an optical disk device, or a tape device.

The input/output device 1840 provides input/output operations for the system 1800. In one implementation, the input/output device 1840 includes a keyboard and/or pointing device. In another implementation, the input/output device 1840 includes a display unit for displaying graphical user interfaces.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

As used herein, the term "real-time" refers to transmitting or processing data without intentional delay given the processing limitations of a system, the time required to accurately obtain data and images, and the rate of change of the data and images. In some examples, "real-time" is used to describe concurrently receiving, cleaning, and interpreting EEG signals. Although there may be some actual delays, such delays generally do not prohibit the signals from being cleaned and analyzed within sufficient time such that the data analysis remains relevant to provide decision-making feedback and accomplish computer-based tasks. For example, adjustments to a smart thermostat are calculated based on user EEG signals. Cleaned signals are analyzed to determine the user's desired temperature before enough time has passed to render the EEG signals irrelevant.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous. Wireless or wired connections may be advantageous for different use cases. Miniaturized components may replace existing components. Other data transmission protocols than those listed may be developed and implemented. The nature of the ML systems used for both data cleaning and classification may change.

What is claimed is:

1. A sensor device, comprising:
   a sensor housing defining a channel extending along a channel axis through the housing from a first side of the sensor housing to a second side of the sensor housing opposite the first side;
   at least one contact electrode extending from the first side of the housing;
   an electrically-conducting lead attached to the housing in electrical communication with the at least one contact electrode; and
   a locking mechanism located in the channel and configured to engage with at least one strand of human hair permitting one-way axial motion of the at least one strand of human hair threaded through the channel from the first side to the second side.

2. The sensor device of claim 1, wherein the locking mechanism comprises a ratchet.

3. The sensor device of claim 2, wherein the ratchet is a linear ratchet.

4. The sensor device of claim 3, wherein the linear ratchet comprises a rack of teeth and one or more pawls that engage the rack of teeth to permit relative motion between the rack of teeth and the at least one strand of human hair in one direction and limit relative motion between the rack of teeth and the at least one strand of human hair in an opposite direction.

5. The sensor device of claim 4, wherein each of the teeth have a first surface with a first slope with respect to an axial direction and a second surface with a second slope with respect to the axial direction, the first slope being greater than the second slope.

6. The sensor device of claim 2, wherein the ratchet is a rotary ratchet.

7. The sensor device of claim 6, wherein the rotary ratchet comprises at least one gear configured to rotate in about a rotary axis orthogonal to the channel axis and at least one pawl arranged to engage the gear to permit the gear to rotate in one direction of rotation and limit rotation in an opposite direction of rotation.

8. The sensor device of claim 2, wherein the device comprises a mechanical release switch arranged to disengage components of the ratchet to permit axial motion of the at least one strand of human hair through the channel from the second side to the first side.

9. The sensor device of claim 1, wherein the locking mechanism comprises an electromechanical actuator arranged to engage the at least one strand of human hair and translate the device relative to the at least one strand of human hair.

10. The sensor device of claim 9, wherein the electromechanical actuator comprises a piezoelectric actuator.

11. The sensor device of claim 9, wherein the electromechanical actuator is a linear actuator.

12. The sensor device of claim 9, wherein the electromechanical actuator is a rotary actuator.

13. The sensor device of claim 9, further comprising a sensor for monitoring contact between the at least one contact electrode and a user's scalp and an electronic processor in communication with the sensor and the electromechanical actuator, the electronic processor being programmed to adjust a position of the sensor device along the at least one strand of human hair based on the monitored contact.

14. The sensor device of claim 13, wherein the electronic processor is programmed to adjust the position to maintain a level of electrical contact between the at least one contact electrode and the user's scalp.

15. The sensor device of claim 1, wherein the at least one contact electrode comprises a plurality of spatially-separated electrical contact points.

16. The sensor device of claim 15, wherein the plurality of spatially-separated electrical contact points are electrically connected in parallel to the electrically-conducting lead.

17. The sensor device of claim 1, further comprising a release mechanism for releasing the locking mechanism to permit disengagement of the sensor device from the at least one strand of human hair.

18. The sensor device of claim 1, wherein the sensor housing comprises a first portion and a second portion,
wherein the first portion is coupled to the second portion by a hinged joint on a first side of the housing, and
wherein the first portion is coupled to the second portion by a locking mechanism on a second side of the housing.

19. A system, comprising:
a bioamplifier; and at least one sensor device, each sensor device comprising:
a sensor housing defining a channel extending along a channel axis through the housing from a first side of the sensor housing to a second side of the sensor housing opposite the first side;
at least one contact electrode extending from the first side of the housing;
an electrically-conducting lead attached to the housing in electrical communication with the at least one contact electrode; and
a locking mechanism located in the channel and configured to engage with at least one strand of human hair permitting one-way axial motion of the at least one strand of human hair threaded through the channel from the first side to the second side,
wherein each of the at least one sensor devices is in electronic communication with the bioamplifier.

20. A sensor device, comprising:
a sensor housing defining a channel extending along a channel axis through the housing from a first side of the sensor housing to a second side of the sensor housing opposite the first side;
at least one contact electrode extending from the first side of the housing;
an electrically-conducting lead attached to the housing in electrical communication with the at least one contact electrode; and
means for locking at least one strand of human hair within the channel by at least engaging with the at least one strand of human hair permitting one-way axial motion of the at least one strand of human hair threaded through the channel from the first side to the second side.

* * * * *